(12) United States Patent
Onozawa et al.

(10) Patent No.: US 11,905,366 B2
(45) Date of Patent: Feb. 20, 2024

(54) METHOD FOR PRODUCING MULTI-ARM TYPE POLYETHYLENE GLYCOL DERIVATIVE

(71) Applicant: NOF CORPORATION, Tokyo (JP)

(72) Inventors: Akihide Onozawa, Kawasaki (JP); Hiroki Yoshioka, Kawasaki (JP); Masaki Kamiya, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 792 days.

(21) Appl. No.: 17/041,102

(22) PCT Filed: Mar. 27, 2019

(86) PCT No.: PCT/JP2019/013306
§ 371 (c)(1),
(2) Date: Sep. 24, 2020

(87) PCT Pub. No.: WO2019/189431
PCT Pub. Date: Oct. 3, 2019

(65) Prior Publication Data
US 2021/0024692 A1  Jan. 28, 2021

(30) Foreign Application Priority Data
Mar. 27, 2018 (JP) ................................ 2018-059150

(51) Int. Cl.
| | | |
|---|---|---|
| A61K 47/60 | (2017.01) | |
| C08G 65/324 | (2006.01) | |
| C08G 65/325 | (2006.01) | |
| C08G 65/326 | (2006.01) | |
| C08G 65/331 | (2006.01) | |
| C08G 65/333 | (2006.01) | |
| C08G 65/334 | (2006.01) | |

(52) U.S. Cl.
CPC ............ *C08G 65/324* (2013.01); *A61K 47/60* (2017.08); *C08G 65/325* (2013.01); *C08G 65/326* (2013.01); *C08G 65/331* (2013.01); *C08G 65/333* (2013.01); *C08G 65/334* (2013.01)

(58) Field of Classification Search
CPC ........ A61K 47/60; C08G 65/02; C08G 65/04; C08G 65/08; C08G 65/324; C08G 2650/58
See application file for complete search history.

(56) References Cited

U.S. PATENT DOCUMENTS

| | | | |
|---|---|---|---|
| 6,300,525 B1 | 10/2001 | Anderson et al. | |
| 6,495,620 B1 | 12/2002 | Jones et al. | |
| 2002/0062034 A1 | 5/2002 | Anderson et al. | |
| 2002/0193473 A1 | 12/2002 | Anderson et al. | |
| 2003/0004238 A1 | 1/2003 | Jones et al. | |
| 2003/0008953 A1 | 1/2003 | Dotson et al. | |
| 2003/0013786 A1 | 1/2003 | Anderson et al. | |
| 2003/0114541 A1 | 6/2003 | Dotson et al. | |
| 2003/0114558 A1 | 6/2003 | Dotson et al. | |
| 2003/0120092 A1 | 6/2003 | Dotson et al. | |
| 2003/0139612 A1 | 7/2003 | Anderson et al. | |
| 2003/0171462 A1 | 9/2003 | Anderson et al. | |
| 2003/0181534 A1 | 9/2003 | Anderson et al. | |
| 2003/0181552 A1 | 9/2003 | Anderson et al. | |
| 2004/0110967 A1 | 6/2004 | Anderson et al. | |
| 2004/0116515 A1 | 6/2004 | Anderson et al. | |
| 2005/0239926 A1 | 10/2005 | Xie et al. | |
| 2005/0239928 A1 | 10/2005 | Xie et al. | |
| 2007/0299256 A1 | 12/2007 | Xie | |
| 2012/0077988 A1 | 3/2012 | Yamamoto et al. | |
| 2012/0322955 A1 | 12/2012 | Yoshioka et al. | |
| 2015/0073155 A1 | 3/2015 | Yoshioka et al. | |
| 2016/0326317 A1 | 11/2016 | Yoshioka et al. | |
| 2017/0107325 A1 | 4/2017 | Tsubusaki et al. | |
| 2017/0312363 A1 | 11/2017 | Weng et al. | |
| 2018/0312466 A1 | 11/2018 | Yamamoto et al. | |
| 2020/0079903 A1 | 3/2020 | Yoshioka et al. | |

FOREIGN PATENT DOCUMENTS

| | | |
|---|---|---|
| CN | 102985462 A | 3/2013 |
| CN | 104245791 A | 12/2014 |
| CN | 106164063 A | 11/2016 |

(Continued)

OTHER PUBLICATIONS

Communication dated Dec. 3, 2021 issued by the European Patent Office in corresponding application No. 19776510.0.
Clayden, J., et al., : "Saturated heterocycles and stereoelectronics" In: "Organic Chemistry", Jan. 1, 2001 (Jan. 1, 2001), pp. 1137-1138 (3 pages).
Terashima et al., "Arm-Cleavable Microgel Star Polymers: A Versatile Strategy for Direct Core Analysis and Functionalization", 2014, Journal of the American Chemical Society, vol. 136, No. 29, 4 pages total.
Communication dated Oct. 10, 2022 by the Chinese Patent Office for corresponding Chinese Patent Application No. 201980021767.3.

(Continued)

*Primary Examiner* — Irina S Zemel
*Assistant Examiner* — Jeffrey S Lenihan
(74) *Attorney, Agent, or Firm* — Sughrue Mion, PLLC

(57) ABSTRACT

A method for producing a multi-arm type polyethylene glycol derivative, which includes carrying out the following in order: Step (A): protecting an even number of hydroxyl groups, while leaving only the hydroxyl group at the 1-position of a polyhydric alcohol having an odd number of hydroxyl groups, other than the hydroxyl group at the 1-position by cyclic benzylidene acetalization, Step (B): linking two molecules of the compound obtained in step (A) to a compound for introducing a specific linker by etherification reaction, Step (C): deprotecting the cyclic benzylidene acetal structure at the terminal of the compound obtained in step (B), Step (D): polymerizing 3 to 600 mol of ethylene oxide to each hydroxyl group of the compound obtained in step (C) to obtain a multi-arm type polyethylene glycol derivative, and Step (E): functionalizing the hydroxyl group at the terminal of the multi-arm type polyethylene glycol derivative obtained in step (D).

3 Claims, No Drawings

(56) References Cited

FOREIGN PATENT DOCUMENTS

| | | |
|---|---|---|
| EP | 2 692 771 A1 | 2/2014 |
| EP | 2 832 765 A1 | 2/2015 |
| JP | 2004-508374 A | 3/2004 |
| JP | 2004-323691 A | 11/2004 |
| JP | 2004-534005 A | 11/2004 |
| JP | 2010-536850 A | 12/2010 |
| JP | 2011-157466 A | 8/2011 |
| JP | 2012-214747 A | 11/2012 |
| JP | 2013-227543 A | 11/2013 |
| WO | 2012/133490 A1 | 10/2012 |
| WO | 2016/050210 A1 | 4/2016 |
| WO | 2018/180917 A1 | 10/2018 |

OTHER PUBLICATIONS

Office Action dated Aug. 18, 2022 by the Japanese Patent Office in counterpart Japanese Patent Application No. 2019-059703.

Office Action dated Apr. 16, 2021, issued by the India Intellectual Property Office in corresponding Indian Patent Application No. 202047041623.

Arthur T. Ness et al., "New Derivatives of 2,3,4,5-Dibenzylidene-D,L-xylitol and 2,4 : 3,5-Dimethylene-L-xylitol", J. Am. Chem. Soc., 1953, vol. 75, pp. 132-134.

International Search Report (PCTISA/210) dated Jul. 2, 2019 by the International Searching Authority in counterpart International Patent Application No. PCT/JP2019/013306.

Written Opinion (PCTISA/237) dated Jul. 2, 2019 by the International Searching Authority in counterpart International Patent Application No. PCT/JP2019/013306.

METHOD FOR PRODUCING MULTI-ARM TYPE POLYETHYLENE GLYCOL DERIVATIVE

CROSS-REFERENCE TO RELATED APPLICATIONS

This application is a National Phase Entry of PCT International Application No. PCT/JP2019/013306 filed Mar. 27, 2019, which claims priority to Japanese Patent Application No. 2018-059150 filed Mar. 27, 2018.

TECHNICAL FIELD

The present invention relates to a method for producing a multi-arm type polyethylene glycol derivative having a narrow molecular weight distribution.

BACKGROUND ART

A drug delivery system (DDS) has been increasingly used in therapeutic applications for various diseases as an ideal administration form of drugs. Especially, there has been widely investigated a development for improving circulation in blood by modifying a drug with polyethylene glycol, and there have been placed on the market drugs in which a cytokine such as interferon or GCSF is modified with polyethylene glycol. Heretofore, in polyethylene glycol derivatives, a type of derivatives having one reactive functional group at a terminal of polyethylene glycol is common but, in recent years, a multi-arm type polyethylene glycol in which plural functional groups are introduced in one molecule has been used. Since the multi-arm type polyethylene glycol has plural reactive points with a drug, there may be mentioned an advantage that a dose of the drug per unit weight can be increased. However, in the case where the polyethylene glycol derivative contains one having a different number of functional groups, there are contained those in which the number of the drugs modified with one molecule of polyethylene glycol is different, so that there arises a problem that the drug is not homogeneous as a pharmaceutical.

In addition, utilizing high water-solubility and biocompatibility of polyethylene glycol, there has been also advanced a development of water-swelling polyethylene glycol hydrogel in which polyethylene glycol and other molecule are combined. Various applications of the polyethylene glycol hydrogel has been investigated in biological and medical fields, for example, adhesive/hemostatic agents, adhesion prevention agents, carriers for drug controlled release, regenerative medical materials, and the like. Also as polyethylene glycol for the hydrogel uses, a multi-arm type having more reactive points is useful for forming a cross-linked structure with the other molecule. Particularly, in the case where the hydrogel is used as a carrier for drug controlled release or a regenerative medical material, a quality of a narrower molecular weight distribution is desired for strictly controlling permeation and a diffusion rate of a drug or a protein as a growth factor of a cell from the gel.

As a raw material for the multi-arm type polyethylene glycol, it is common to use a polyhydric alcohol corresponding to the desired number of functional groups. For example, ring-opening polymerization of ethylene oxide is conducted using glycerin or the like for a three-arm type or pentaerythritol or the like for a four-arm type as a raw material. Since these low-molecular-weight raw materials hardly contain impurities, it is possible to form polyethylene glycol of a high quality having a relatively narrow molecular weight distribution. On the other hand, as six-arm type and eight-arm type polyethylene glycols, there have been known those using a polyglycerol such as tetraglycerin or hexaglycerin as a low-molecular-weight raw material. The polyglycerol is usually a mixture containing ones having plural degrees of polymerization and/or isomers. Since it is difficult to purify the mixture into a single component owing to high polarity, a multi-arm type polyethylene glycol of a low quality having a wide molecular weight distribution is formed when ethylene oxide is added thereto. Therefore, there is a need for a method for producing a multi-arm type polyethylene glycol derivative having a narrower molecular weight distribution even in a more branched type.

As such a highly pure 8-arm type polyethylene glycol derivative, Patent Literature 1 describes a multi-arm type polyethylene glycol derivative having a narrow molecular weight distribution. In the method for producing a multi-arm type polyethylene glycol derivative described in the literature, the low-molecular-weight compound to which ethylene oxide is added uses as a raw material a compound obtained by protecting the hydroxyl group of a polyhydric alcohol such as xylitol or volemitol by isopropylidene acetalization. However, although not specified in Patent Literature 1, in the case of isopropylidene acetalization of the hydroxyl group of such a polyhydric alcohol, an isomer is generally produced as a by-product and therefore, in Patent Literature 2, the isomer is removed by purification such as distillation or column chromatography. As described above, in the method of isopropylidene acetalization of the hydroxyl group of a polyhydric alcohol, an isomer is produced as a by-product, and a multistep purification process is required to remove it, resulting in a large reduction in yield. Therefore, further improvement is necessary for industrial production.

Non-Patent Literature 1 describes the protection of xylitol by benzylidene acetalization. In the protection of xylitol by benzylidene acetalization, the isomer generated by isopropylidene acetalization is not produced as a by-product and, while leaving the hydroxyl group at the 1-position, other hydroxyl groups can be protected. However, the literature describes only the protection of xylitol, and does not describe the reaction of synthesizing a multi-arm type polyethylene glycol derivative using a protected body as a raw material. Furthermore, since the solubility of the benzylidene acetalized xylitol is extremely low and it hardly dissolves in water or an organic solvent, it is very difficult to efficiently convert the hydroxyl group at the 1-position by a reaction.

PRIOR ART DOCUMENT

Non-Patent Literature

Non-Patent Literature 1: Arthur T. Ness, Raymond M. Hann, C. S. Hudson, J. Am. Chem. Soc., 75, 132-134 (1953)

Patent Literature

Patent Literature 1: JP-A-2013-227543
Patent Literature 2: JP-A-2012-214747

SUMMARY OF INVENTION

Problem to be Solved by the Invention

An object of the present invention is to provide a method capable of industrially producing a highly pure multi-arm type polyethylene glycol derivative having a narrow molecular weight distribution, which is suitable for use as a material in DDS and biological and medical fields, in good yield.

Means for Solving the Problem

As a result of extensive studies for attaining the above object, the present inventors have established a method for producing a multi-arm type polyethylene glycol derivative having the following constitution.

Thus, the present invention is as follows.

(1) A method for producing a multi-arm type polyethylene glycol derivative represented by the following formula (1), wherein the following step (A), step (B), step (C), step (D), and step (E) are carried out in this order:

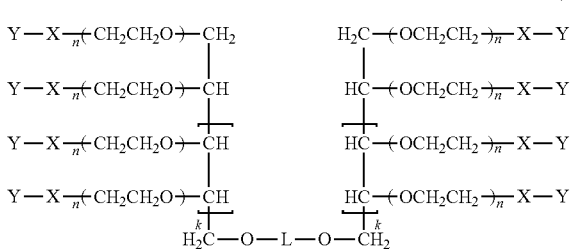

(1)

wherein, in the formula (1),
L is a group selected from the group consisting of a linear or branched alkylene group having 3 to 8 carbon atoms, a substituted or unsubstituted arylene group having 6 to 12 carbon atoms and a cycloalkylene group having 6 to 12 carbon atoms,
k represents 1 or 2,
n represents an average molar number of oxyethylene groups added and n represents an integer between 3 and 600,
X represents an alkylene group which may have a single bond, an ester bond, a urethane bond, an amide bond, an ether bond, a carbonate bond, a secondary amino group, a urea bond, a thioether bond, or a thioester bond in the chain or at the terminal, and
Y represents a chemically reactive functional group;
Step (A): a step of protecting an even number of hydroxyl groups, while leaving only the hydroxyl group at the 1-position of a polyhydric alcohol having an odd number of hydroxyl groups, other than the hydroxyl group at the 1-position by cyclic benzylidene acetalization,
Step (B): a step of linking two molecules of the compound obtained in the step (A) to a compound represented by the following formula (2) by an etherification reaction:

A-L-A (2)

wherein, in the formula (2),
L represents a group selected from the group consisting of a linear or branched alkylene group having 3 to 8 carbon atoms, a substituted or unsubstituted arylene group having 6 to 12 carbon atoms and a cycloalkylene group having 6 to 12 carbon atoms, and
A represents a halogen atom selected from chlorine, bromine, or iodine or a sulfone-based leaving group,
Step (C): a step of deprotecting the cyclic benzylidene acetal structure at the terminal of the compound obtained in the step (B), where 8 hydroxyl groups are formed in the case of k=1 and 12 hydroxyl groups are formed in the case of k=2,
Step (D): a step of polymerizing 3 to 600 mol of ethylene oxide to each hydroxyl group of the compound obtained in the step (C) to obtain a multi-arm type polyethylene glycol derivative, and
Step (E): a step of functionalizing the hydroxyl group at the terminal of the multi-arm type polyethylene glycol derivative obtained in the step (D).

(2) The method according to (1), wherein the step (A) is carried out using an acidic solution as a solvent.

(3) The method according to (1), wherein the compound obtained in the step (B) is purified by recrystallization.

(4) The method according to (1), wherein the step (C) is carried out under an acidic condition.

Effect of the Invention

The present invention is a novel method for producing a multi-arm type polyethylene glycol derivative that is suitable for use as a material in new biological and medical fields without limiting to DDS. In this production method, an even number of hydroxyl groups can be efficiently protected by benzylidene acetalization while leaving the hydroxyl group at the 1-position of a polyhydric alcohol such as xylitol or volemitol as a raw material. Since the compound in which the protected bodies are bonded with a linker has extremely high crystallinity, the compound can be purified only by recrystallization without requiring specific purification, as compared with the route through the conventional isopropylidene-protected body. Thereafter, the removal of the benzylidene acetal can afford a low-molecular-weight raw material that contains almost no impurities having different number of functional groups. In addition, a highly pure multi-arm type polyethylene glycol derivative can be obtained by polymerizing ethylene oxide to a low-molecular-weight raw material. Then, it is possible to obtain a multi-arm type polyethylene glycol derivative that can effectively modify a plurality of drugs through functionalization of the hydroxyl group at the terminal of the obtained polyoxyethylene chain and can be used as a hydrogel.

MODES FOR CARRYING OUT THE INVENTION

The multi-arm type polyethylene glycol derivative according to the invention is represented by the following formula (1).

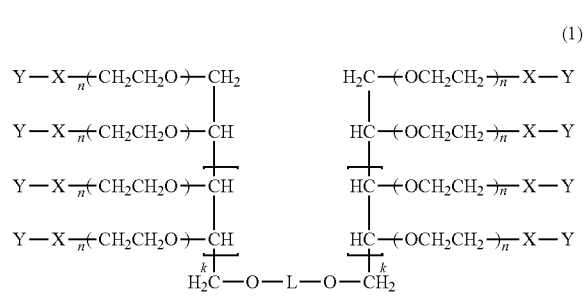

(1)

L in the formula (1) of the invention represents a group selected from a linear or branched alkylene group having 3 to 8 carbon atoms, a substituted or unsubstituted arylene group having 6 to 12 carbon atoms, and a cycloalkylene group having 6 to 12 carbon atoms.

As the alkylene group, an alkylene group having 3 to 8 carbon atoms may be mentioned. Specific examples thereof include, for example, an ethylene group, a propylene group, an isopropylene group, an n-butylene group, an s-butylene group, a t-butylene group, a pentamethylene group, a hexamethylene group, a heptamethylene group, an octamethylene group, and the like. Further, the arylene group is a substituted or unsubstituted arylene group having 6 to 12 carbon atoms and, for example, a phenylene group, a naphthylene group, an anthrylene group, and the like may be mentioned. Moreover, as the cycloalkylene group, a cycloalkylene group having 6 to 12 carbon atoms may be mentioned and specific examples thereof include, for example, a cyclohexylene group, a cycloheptylene group, a cyclooctylene group, a cyclononylene group, a cyclodecylene group, and the like. In the case where L has less than three carbon atoms, since the effect as a hydrophobic group is not exhibited, the low-molecular-weight raw material is not dispersed in an organic solvent at the time when ethylene oxide is added and thus there is a concern that a molecular weight distribution is broadened. Moreover, in the case where L has more than 12 carbon atoms, since surface active ability of the molecule increases, there is a concern that an expected performance is not exhibited in the case where an application as a pharmaceutical modifier is considered. L is preferably a propylene group, an isopropylene group, an n-butylene group, an s-butylene group, a t-butylene group, a pentamethylene group, a hexamethylene group, a heptamethylene group, or an octamethylene group, and more preferably an n-butylene group.

k in the formula (1) represents 1 or 2, and is preferably 1. The case where k is 1 indicates a xylitol structure, and the case where k is 2 indicates a volemitol structure.

n is an average molar number of oxyethylene groups added and n is usually from 3 to 600, preferably from 5 to 300, and more preferably from 12 to 250.

The molecular weight of the compound of the formula (1) which is preferably used is from 1,500 to 160,000, preferably from 4,000 to 140,000

X is a linker between a polyoxyethylene group and a reactive functional group Y. There is a case where the linker is not present and the case is defined as a single bond. These are not particularly limited so far as they are conjugated bonds and may be any one so far as they are bonds usually used as linkers but there may be preferably mentioned an alkylene group alone or an alkylene group which may have an ether bond, an ester bond, a urethane bond, an amide bond, a carbonate bond, a secondary amino group, a urea bond, a thioether bond or a thioester bond in the alkylene chain or at a terminal thereof. The number of carbon atoms of the alkylene group is preferably from 1 to 12.

As a preferable example of the alkylene group, a structure like (x1) may be mentioned. As a preferable example of the alkylene group having an ether bond, a structure like (x2) may be mentioned. As a preferable example of the alkylene group having an ester bond, a structure like (x3) may be mentioned. As a preferable example of the alkylene group having a urethane bond, a structure like (x4) may be mentioned. As a preferable example of the alkylene group having an amide bond, a structure like (x5) may be mentioned. As a preferable example of the alkylene group having a carbonate bond, a structure like (x6) may be mentioned. As a preferable example of the alkylene group having a secondary amino group, a structure like (x7) may be mentioned. As a preferable example of the alkylene group having a urea bond, a structure like (x8) may be mentioned. As a preferable example of the alkylene group having a thioether bond, a structure like (x9) may be mentioned. As a preferable example of the alkylene group having a thioester bond, a structure like (x10) may be mentioned.

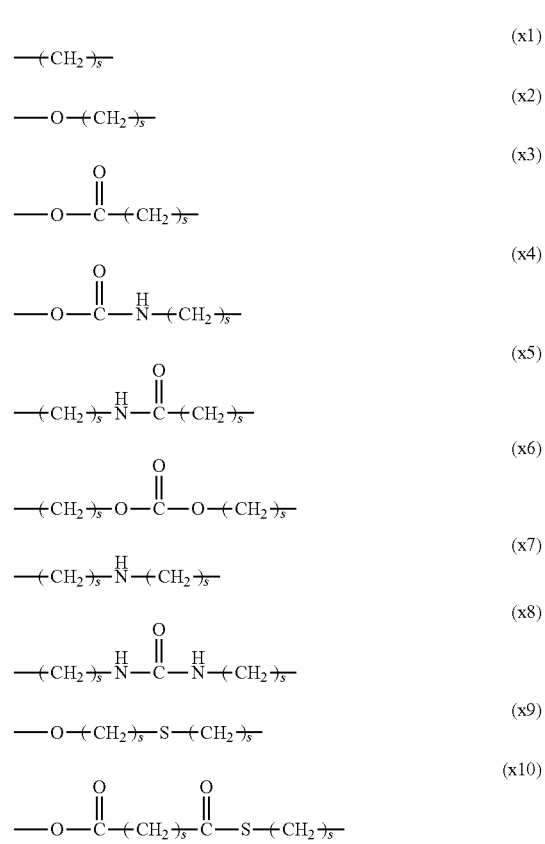

In each formula, s is an integer of 0 to 12. The range of s is from 0 to 12. For example, in the case where it is intended to perform bonding under a hydrophobic environment like the inside of a protein, s is preferably larger one and, in the case where it is intended to perform bonding under a hydrophilic environment, s is preferably smaller one. The symbols s in (x5), (x6), (x7), (x8), (x9), and (x10) may be the same or different.

Y represents a functional group capable of chemical reaction and is preferably a functional group capable of reacting with a hydroxyl group, an amino group, a mercapto group, an aldehyde, a carboxyl group, a triple bond, or an azido group to form a chemical bond with another substance. For example, there may be mentioned functional groups described in "POLY(ETHYLENE GLYCOL) CHEMISTRY" written by J. Milton Harris, "Bioconjugate Techniques second edition" (2008) written by Greg T. Hermanson, and "Pegylated Protein Drug: basic Science and Clinical Application" (2009) written by Francesco M. Veronese, and the like.

Further specifically, there may be mentioned functional groups including a carboxylic acid, an active ester, an active carbonate, an aldehyde, an amine, an oxyamine, a hydrazide, an azide, an unsaturated bond, a thiol, a dithiopyridine, a sulfone, a maleimide, a vinylsulfone, an α-iodoacetyl, an acrylate, an isocyanate, an isothiocyanate, an epoxide), and the like.

Preferably, Y is a group shown below.

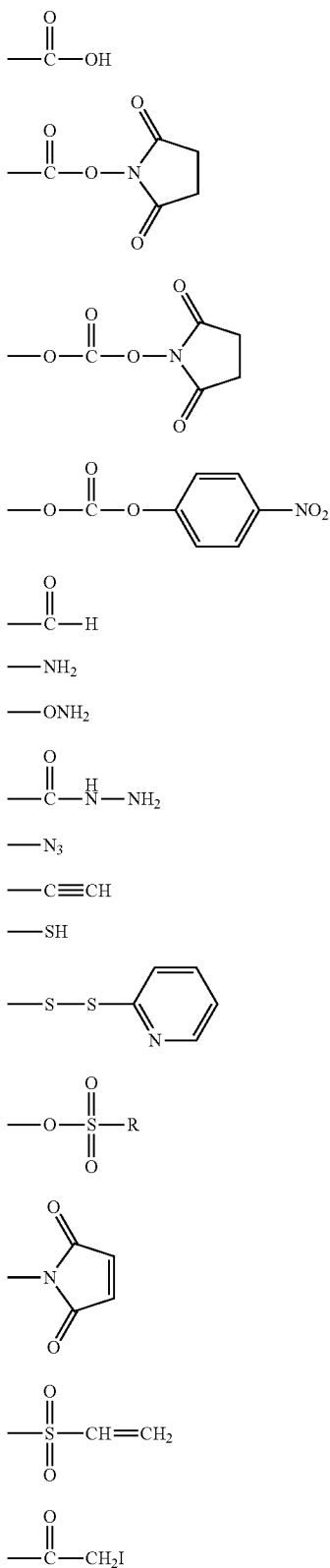

wherein R represents a hydrocarbon group having 1 to 10 carbon atoms, which may contain a fluorine atom.

In preferable embodiments in the reaction of the compound of the invention with another substance, Y is a group represented by the following group (i), (ii), (iii), (iv), (v), or (vi).

Group (i): a functional group capable of reacting with a hydroxyl group of the other substance
(a), (b), (c), (m) mentioned above Group (ii): a functional group capable of reacting with an amino group of the other substance
(a), (b), (c), (d), (e), (m), (n) mentioned above Group (iii): a functional group capable of reacting with a mercapto group of the other substance
(a), (b), (c), (d), (e), (j), (k), (l), (m), (n), (o), (p) mentioned above Group (iv): a functional group capable of reacting with an aldehyde or carboxyl group of the other substance
(f), (g), (h), (k) mentioned above Group (v): a functional group capable of reacting with a triple bond of the other substance
(f), (g), (h), (i), (k) mentioned above Group (vi): a functional group capable of reacting with an azido group of the other substance
(j) mentioned above The multi-arm type polyethylene glycol derivative of the invention can be produced, for example, by performing steps (A), (B), (C), (D), and (E) in the order as follows.

The step (A) is a step of protecting an even number of hydroxyl groups, while leaving only the hydroxyl group at the 1-position of a polyhydric alcohol having an odd number of hydroxyl group, by cyclic benzylidene acetalization.

The step (B) is a step of linking two molecules of the compound obtained in the step (A) to a compound represented by the following formula (2) by an etherification reaction:

$$A\text{-}L\text{-}A \quad (2)$$

wherein, in the formula (2), L represents a group selected from the group consisting of a linear or branched alkylene group having 3 to 8 carbon atoms, a substituted or unsubstituted arylene group having 6 to 12 carbon atoms and a cycloalkylene group having 6 to 12 carbon atoms, and A represents a halogen atom selected from chlorine, bromine, or iodine or a sulfone-based leaving group.

The step (C) is a step of deprotecting the cyclic benzylidene acetal structure at the terminal of the compound obtained in the step (B), where 8 hydroxyl groups are formed in the case of k=1 and 12 hydroxyl groups are formed in the case of k=2.

The step (D) is a step of polymerizing 3 to 600 mol of ethylene oxide to each hydroxyl group of the compound obtained in the step (C) to obtain a multi-arm type polyethylene glycol derivative.

The step (E) is a step of functionalizing the hydroxyl group at the terminal of the multi-arm type polyethylene glycol derivative obtained in the step (D).

By performing the above steps (A), (B), (C), (D) and (E), the polyoxyethylene derivative (1) represented by the formula (1) is produced.

Hereinafter, preferred specific examples of the method for producing the multi-arm type polyethylene glycol derivative (1) will be further described. Since the derivative can be produced by the same production method in both cases of k=1 and k=2, the method will be described with regard to a derivative of k=1, i.e., a multi-arm type polyethylene glycol derivative represented by the following formula (3) (multi-arm type polyethylene glycol derivative (3)).

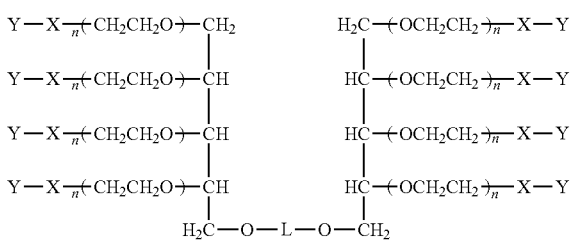

(3)

wherein, in the formula (3), L, X, Y, and n have the same meanings as described above.

The multi-arm type polyethylene glycol derivative (3) can be produced by carrying out the following steps (A), (B), (C), (D) and (E) in this order.

The step (A) is a step of protecting four hydroxyl groups, while leaving only the hydroxyl group at the 1-position of xylitol having five hydroxyl groups, by cyclic benzylidene acetalization. In this step, highly pure 2,3,4,5-dibenzylidenexylitol can be obtained. 1,2,4,5-Dibenzylidenexylitol, which is an isomer in which a hydroxyl group at the 3-position remains, is not produced in the step (A).

The method of acetalization is not particularly limited as far as it is a general hydroxyl group protection method as described in PROTECTIVE GROUPS IN ORGANIC SYNTHESIS (THEODORA W. GREENE et al) and the like. Specifically, 2,3,4,5-dibenzylidenexylitol can be obtained by reacting xylitol with benzaldehyde in the presence of an acid catalyst such as sulfuric acid, hydrochloric acid, phosphoric acid, p-toluenesulfonic acid, or p-toluenesulfonic acid monohydrate.

The amount of the acid to be used is preferably $5\times10^{-6}$ to $5\times10^{-3}$ equivalents, more preferably $5\times10^{-5}$ to $5\times10^{-4}$ equivalents to xylitol.

Further, in order to dissolve xylitol, a large amount of the acid may be used as a solvent, and in that case, the amount is preferably from 5 to 100 times by weight, more preferably from 10 to 50 times by weight, relative to xylitol. As the type of the acid, sulfuric acid, hydrochloric acid or phosphoric acid may be mentioned and it is preferably sulfuric acid or hydrochloric acid, and more preferably sulfuric acid.

The amount of benzaldehyde to be used is preferably from 2.0 to 5.0 equivalents, and more preferably from 2.5 to 4.0 equivalents to xylitol.

In the reaction, a solvent such as dimethylformamide, tetrahydrofuran or dichloromethane can be used, and dimethylformamide or tetrahydrofuran is preferable.

The reaction temperature is usually from 0 to 60° C., preferably from 10 to 50° C. The reaction time is preferably from 3 to 24 hours. When the reaction time is short, the reaction becomes insufficient.

In the reaction, it is preferable to remove xylitol that has not been acetalized, impurities and the like. The 2,3,4,5-dibenzylidenexylitol formed in the reaction crystallizes in the reaction solution and thus can be purified simply by filtration. Since the obtained crystals have low solubility in any solvent, impurities can be removed by suspending and stirring the crystals in a solvent and repeating filtration, as a method of further increasing the purity. As the solvent to be used for this suspension washing, solvents such as water, methanol, ethanol, diethyl ether, methyl t-butyl ether, THF (tetrahydrofuran), and acetonitrile are preferable, and a mixed solution thereof may be used. The washing temperature is usually from 0 to 60° C., preferably from 10 to 50° C. The stirring time is preferably from 10 minutes to 3 hours. When the stirring time is short, the purification becomes insufficient.

The step (B) is not particularly limited, but is preferably an etherification step by the Williamson reaction between two molecules of 2,3,4,5-dibenzylidenexylitol and the compound (2).

In the compound (2) of the reaction, A is sufficiently a leaving group, and examples thereof include a halogen atom such as chlorine, bromine or iodine, or a sulfone-based leaving group such as a methanesulfonyl group, a p-toluenesulfonyl group or a trifluoromethanesulfonyl group. As the base for the etherification, it is sufficient that an alkali metal alkoxide salt is formed, and there may be mentioned potassium t-butoxide, sodium hydride, potassium hydride, metallic sodium, hexamethyldisilazane, potassium carbonate and the like. L represents a group selected from a linear or branched alkylene group having 3 to 8 carbon atoms, a substituted or unsubstituted arylene group having 6 to 12 carbon atoms, and a cycloalkylene group having 6 to 12 carbon atoms. As the alkylene group, an alkylene group having 3 to 8 carbon atoms may be mentioned. Specific examples thereof include, for example, an ethylene group, a propylene group, an isopropylene group, an n-butylene group, an s-butylene group, a t-butylene group, a pentamethylene group, a hexamethylene group, a heptamethylene group, an octamethylene group, and the like. Further, the arylene group is a substituted or unsubstituted arylene group having 6 to 12 carbon atoms and, for example, a phenylene group, a naphthylene group, an anthrylene group, and the like may be mentioned. Moreover, as the cycloalkylene group, a cycloalkylene group having 5 to 12 carbon atoms may be mentioned and specific examples thereof include, for example, a cyclohexylene group, a cycloheptylene group, a cyclooctylene group, a cyclononylene group, a cyclodecylene group, and the like. In the case where L has less than three carbon atoms, since the effect as a hydrophobic group is not exhibited, the low-molecular-weight raw material is not dispersed in an organic solvent at the time when ethylene oxide is added and thus there is a concern that a molecular weight distribution is broadened. Moreover, in the case where L has more than 12 carbon atoms, since surface active ability of the molecule increases, there is a concern that an expected performance is not exhibited in the case where an application as a pharmaceutical modifier is considered. L is preferably a propylene group, an isopropylene group, an n-butylene group, an s-butylene group, a t-butylene group, a pentamethylene group, a hexamethylene group, a heptamethylene group, or an octamethylene group, and more preferably an n-butylene group. The reaction solvent is not particularly limited as far as it is an aprotic solvent, and there may be mentioned tetrahydrofuran, dimethyl ether, methylene chloride, chloroform, dimethylformamide, toluene, benzene and the like, and it is more preferably toluene or dimethylformamide.

The crystals obtained by this reaction can be purified by recrystallization. As the solvent to be used for recrystallization, a solvent such as tetrahydrofuran or dimethylformamide can be used, and dimethylformamide is preferable.

The amount of the solvent to be used for recrystallization is preferably from 9 to 30 times by weight, more preferably from 18 to 26 times by weight, relative to the compound (2). The temperature for recrystallization is from −10° C. to 20° C., preferably from 0° C. to 10° C. When the temperature exceeds 20° C., the formation of crystals becomes insufficient and the yield may decrease. The time for recrystallization is preferably 1 hour or more. When the time is less than 1 hour, the removal of impurities may be insufficient.

Step (C) is a step of deprotecting the cyclic benzylidene acetal structure at the terminal of the compound obtained by the etherification of step (B).

The method for deprotecting the cyclic acetal is not particularly limited as far as it is such a general deprotection method as described in PROTECTIVE GROUPS IN ORGANIC SYNTHESIS (THEODORA W. GREENE et al) and the like, but specifically, it can be deprotected in the presence of an acid catalyst. As the acid catalyst, acetic acid, hydrochloric acid, phosphoric acid, p-toluenesulfonic acid, trifluoroacetic acid and the like may be mentioned, and it is preferably hydrochloric acid, phosphoric acid or trifluoroacetic acid, and more preferably trifluoroacetic acid.

The amount of the acid to be used is preferably from 0.05 to 2 times by weight, more preferably from 0.1 to 1 time by weight, relative to the compound obtained in the step (B). The solvent to be used in the deprotection reaction is water, methanol, ethanol, acetonitrile, tetrahydrofuran, dioxane, dimethylsulfoxide, dimethylformamide or dimethylacetamide, and water or methanol is preferable. The amount of the solvent to be used is from 1 to 50 times by weight, preferably from 2 to 35 times by weight, and more preferably from 5 to 20 times by weight, relative to the compound obtained in the step (B).

The reaction time is preferably from 1 to 24 hours. When it is shorter than 1 hour, the deprotection reaction becomes insufficient. The reaction temperature is usually from 0 to 60° C., preferably from 10 to 40° C.

Step (D) is an addition polymerization step of ethylene oxide to the compound having hydroxyl groups newly formed by the deprotection of the cyclic acetal structure. Without no particular limitation, it can be preferably produced through the following step (D1) and subsequent step (D2).

The step (D1) is a step of dissolving the deprotected compound mentioned above in an aqueous solution containing preferably from 50 mol % to 250 mol % of an alkali catalyst, then adding an organic solvent thereto, and conducting azeotropic dehydration at preferably from 50 to 130° C.

The step (D2) is a step of reacting the deprotected compound with ethylene oxide in the presence of an organic solvent at preferably 50 to 130° C. to obtain a multi-arm type polyethylene glycol derivative having a hydroxyl group at the terminal.

The alkali catalyst in the step (D1) is not particularly limited, but there may be mentioned metal sodium, metal potassium, sodium hydride, potassium hydride, sodium hydroxide, potassium hydroxide, sodium methoxide, potassium methoxide and the like. As the solvent for dissolving the alkali catalyst, a protic polar solvent such as methanol or ethanol can be used other than water. The concentration of the alkali catalyst is preferably from 50 mol % to 250 mol %, relative to the deprotected compound mentioned above. When it is less than 50 mol %, the polymerization reaction rate of ethylene oxide is decreased and thermal history is increased to form impurities such as terminal vinyl ether bodies and the like, so that it is advantageous to control the concentration to 50 mol % or more for producing a high-quality high-molecular-weight compound. When the catalyst exceeds 250 mol %, viscosity of the reaction solution is increased or the solution is solidified at the alcoholate formation reaction, so that the stirring efficiency is decreased and there is a tendency that the alcoholate formation is not promoted.

The organic solvent for the azeotropic dehydration is not particularly limited so far as it is an aprotic solvent such as toluene, benzene, xylene, acetonitrile, ethyl acetate, tetrahydrofuran, chloroform, methylene chloride, dimethyl sulfoxide, dimethylformamide, or dimethylacetamide but toluene having a boiling point close to that of water is preferred. Azeotropic temperature is preferably from 50 to 130° C. When the temperature is lower than 50° C., viscosity of the reaction solution increases and moisture tends to remain. Since the remaining of moisture forms a polyethylene glycol compound derived from the moisture, the molecular weight distribution is broadened and there is a concern that the quality is lowered. Also, when the temperature is higher than 130° C., there is a concern that a condensation reaction occurs. In the case where the moisture remains, it is preferred to repeat the azeotropic dehydration repeatedly.

The step (D2) is conducted in an organic solvent. The reaction solvent is not particularly limited so far as it is an aprotic solvent such as toluene, benzene, xylene, acetonitrile, ethyl acetate, tetrahydrofuran, chloroform, methylene chloride, dimethyl sulfoxide, dimethylformamide or dimethylacetamide, but toluene is preferred, which is easily removable by crystallization and vacuum drying after the reaction. The reaction time is preferably from 1 to 24 hours. When the time is shorter than 1 hour, there is a concern that the catalyst is not completely dissolved. When the time is longer than 24 hours, there is a concern that the aforementioned decomposition reaction occurs.

The reaction temperature is preferably from 50 to 130° C. When the temperature is lower than 50° C., the rate of the polymerization reaction is low and the thermal history is increased, so that the quality of the multi-arm type polyethylene glycol derivative having a hydroxyl group at the terminal tends to be lowered. Moreover, when the temperature is higher than 130° C., side reactions such as vinyl etherification of the terminal occur during the polymerization and the quality of the multi-arm type polyethylene glycol derivative having a hydroxyl group at the terminal tends to be lowered. During the polymerization, since the viscosity of the reaction solution is increased as the molecular weight is increased, an aprotic solvent, preferably toluene may be appropriately added.

The step (D2) may be repeated plural times. In that case, the step may be conducted under a similar condition to the above-described condition with adding ethylene oxide to the reaction mixture that remains in the reaction vessel. By controlling the number of repetitions, the average molar number n of oxyethylene groups added can be controlled.

With regard to the compound (3) of the invention, polydispersity $Mw/Mn$ from the starting point of elution until the final point of elution satisfies the relationship of $Mw/Mn \leq 1.05$ when gel permeation chromatography is conducted. More preferred is the case where it satisfies $Mw/Mn \leq 1.03$.

In the case of $Mw/Mn > 1.05$, a polyethylene glycol different in the number of arms is contained and/or ethylene oxide addition does not homogeneously take place, so that the case means that the product is a compound having a broad molecular weight distribution. There is a concern that the case causes a side effect as a pharmaceutical and a biomaterial because the number of modifications with a bio-related substance in one molecule of polyethylene glycol is different in the case of bonding to the bio-related substance and because strict control of permeation and/or diffusion rate of a substance becomes difficult in the case of using the compound as a raw material of a carrier for drug controlled release or a hydrogel of a regeneration medical material.

The step (E) is a step of functionalizing the hydroxyl group at the terminal of the multi-arm type polyethylene glycol derivative obtained in the step (D).

The following describe methods for introducing a functional group into the hydroxyl group at the terminal of the multi-arm type polyethylene glycol derivative in detail. In the following description, the compounds (3) in which functional groups Y are (a) to (p) are sometimes designated as (a) body to (p) body, respectively or "amine body (f)" and the like with attaching the name of the functional group.

[Production Method of Compound (3) in Which Y is (d) or (m)]

A p-nitrophenyl carbonate body (d) or a sulfonate body (m) can be obtained by reacting the hydroxyl group at the terminal of the multi-arm type polyethylene glycol derivative with an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide and either of the compounds represented by the following general formulae (d1) and (m1) in an aprotic solvent such as toluene, benzene, xylene, acetonitrile, ethyl acetate, diethyl ether, t-butyl methyl ether, tetrahydrofuran, chloroform, methylene chloride, dimethyl sulfoxide, dimethylformamide, or dimethylacetamide or in no solvent. Also, the above organic base or inorganic base may not be used. The use ratio of the organic base or inorganic base is not particularly limited but is preferably molar equivalent or more to the hydroxyl group at the terminal of the multi-arm type polyethylene glycol derivative. Moreover, an organic base may be used as a solvent. W in (d1) or (m1) is a halogen atom selected from chlorine, bromine, and iodine and is preferably chlorine. The use ratio of the compound represented by the general formula (d1) or (m1) is not particularly limited but is preferably molar equivalent or more to the hydroxyl group at the terminal of the multi-arm type polyethylene glycol derivative, and further preferably, it is preferred to react the compound in the range of molar equivalent to 50 mol. The reaction temperature is preferably from 0 to 300° C., further preferably from 20 to 150° C. The reaction time is preferably from 10 minutes to 48 hours, further preferably from 30 minutes to 24 hours. The formed compound may be purified by a purification method such as extraction, recrystallization, adsorption treatment, reprecipitation, column chromatography, or supercritical extraction.

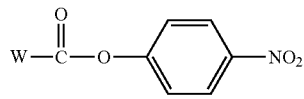

(d1)

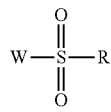

(m1)

wherein W represents a halogen atom selected from chlorine, bromine, and iodine; and R represents a hydrocarbon group having 1 to 10 carbon atoms, which may contain a fluorine atom.

[Production Method of Compound (3) in Which Y is (o)]

A divinyl sulfone body (o) can be obtained by reacting the hydroxyl group at the terminal of the multi-arm type polyethylene glycol derivative with divinyl sulfone in an aprotic solvent such as toluene in the presence of a base catalyst. The base catalyst may be either an inorganic base or an organic base and is not particularly limited and examples thereof include potassium t-butoxide, sodium hydride, potassium hydride, metal sodium, hexamethyldisilazane, potassium carbonate, and the like. The use ratio of the base catalyst is not particularly limited but it is preferably used in the range of 0.1 to 50 mol to the hydroxyl group at the terminal of the multi-arm type polyethylene glycol derivative. The use ratio of divinyl sulfone is not particularly limited but is preferably molar equivalent or more to the hydroxyl group at the terminal of the multi-arm type polyethylene glycol derivative and, for preventing the formation of a by-product dimmer, it is preferred to use it an excess amount of 10 equivalents or more. The reaction temperature is preferably from 0 to 100° C., further preferably from 20 to 40° C. The reaction time is preferably from 10 minutes to 48 hours, further preferably from 30 minutes to 24 hours. The formed compound may be purified by a purification method such as extraction, recrystallization, adsorption treatment, reprecipitation, column chromatography, or supercritical extraction.

[Production Method of Compound (3) in Which Y is (a)]

A carboxyl body (a) can be obtained by reacting the hydroxyl group at the terminal of the multi-arm type polyethylene glycol derivative or an amine body (f) to be mentioned below with a dicarboxylic acid anhydride such as succinic anhydride or glutaric anhydride in an aforementioned aprotic solvent or no solvent. The use ratio of the dicarboxylic acid anhydride is not particularly limited but is preferably molar equivalent or more, further preferably molar equivalent to 5 mol to the hydroxyl group at the terminal of the multi-arm type polyethylene glycol derivative. The reaction temperature is preferably from 0 to 200° C., further preferably from 20 to 150° C. The reaction time is preferably from 10 minutes to 48 hours, further preferably from 30 minutes to 12 hours.

For the reaction, there may be used an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide as a catalyst. The use ratio of the catalyst is not particularly limited but is preferably from 0.1 to 50% by mass, further preferably from 0.5 to 20% by mass to the hydroxyl group at the terminal of the multi-arm type polyethylene glycol derivative. The thus formed compound may be purified by a purification method such as extraction, recrystallization, adsorption treatment, reprecipitation, column chromatography, or supercritical extraction or, in the case of using the compound as a raw material of a condensation reaction, it may be used as it is.

Also, the carboxyl body (a) can be obtained by reacting the hydroxyl group at the terminal of the multi-arm type polyethylene glycol derivative with a halogen-substituted carboxylic acid ester such as ethyl 6-bromohexanoate or ethyl 7-bromoheptanoate in an aforementioned aprotic solvent or no solvent. The use ratio of the halogen-substituted carboxylic acid ester is not particularly limited but is preferably molar equivalent or more, further preferably molar equivalent to 30 mol to the hydroxyl group at the terminal of the multi-arm type polyethylene glycol derivative. The reaction temperature is preferably from 0 to 200° C., further preferably from 20 to 150° C. The reaction time is preferably from 10 minutes to 48 hours, further preferably from 30 minutes to 12 hours. For the reaction, there may be used an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide as a catalyst. The use ratio of the catalyst is preferably from 0.1 to 500% by mass, further preferably from 0.5 to 300% by mass, relative to the hydroxyl group at the terminal of the multi-arm type polyethylene glycol derivative. After etherification, an aqueous solution of sodium hydroxide, potassium hydroxide or the like in the case of the organic base or water in the case of the inorganic base is added, and thus hydrolysis of the ester is conducted. The reaction temperature is preferably from 0 to 100° C., further preferably from 20 to 100° C. The reaction time is preferably from 10 minutes to 48 hours, further preferably from 30 minutes to 12 hours. After the reaction, neutralization is conducted with hydrochloric acid, sulfuric acid, or the like. The thus formed compound may be purified by an aforementioned purification method or, in the case of using the compound as a raw material of a condensation reaction, it may be used as it is.

[Production Method of Compound (3) in Which Y is (b)]

A succinimide body (b) can be obtained by subjecting the carboxyl body (a) to a condensation reaction with N-hydroxysuccinimide in an aforementioned aprotic solvent or no solvent in the presence of a condensing reagent such as DCC (dicyclohexylcarbodiimide) or EDC (1-ethyl-3-(3-dimethylaminopropyl)carbodiimide). The condensing agent is not particularly limited but is preferably DCC. The use ratio of DCC is preferably molar equivalent or more, further preferably molar equivalent to 5 mol to the carboxyl group. The use ratio of N-hydroxysuccinimide is preferably molar equivalent or more, further preferably molar equivalent to 5 mol to the carboxyl group. The reaction temperature is preferably from 0 to 100° C., further preferably from 20 to 80° C. The reaction time is preferably from 10 minutes to 48 hours, further preferably from 30 minutes to 12 hours. The formed compound may be purified by a purification method such as extraction, recrystallization, adsorption treatment, reprecipitation, column chromatography, or supercritical extraction.

[Production Method of Compound (3) in Which Y is (c)]

A succinimide carbonate body (c) can be obtained by reacting the hydroxyl group at the terminal of the multi-arm type polyethylene glycol derivative with an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide and N,N'-disuccinimide carbonate in an aforementioned aprotic solvent or in no solvent. The above-described organic base or inorganic base may not be used. The use ratio of the organic base or inorganic base is not particularly limited but is preferably molar equivalent or more to the hydroxyl group at the terminal of the multi-arm type polyethylene glycol derivative. Moreover, the organic base may be used as a solvent. The use ratio of N,N'-disuccinimide carbonate is preferably molar equivalent or more, further preferably molar equivalent to 5 mol to the hydroxyl group at the terminal of the multi-arm type polyethylene glycol derivative. The reaction temperature is preferably from 0 to 100° C., further preferably from 20 to 80° C. The reaction time is preferably from 10 minutes to 48 hours, further preferably from 30 minutes to 12 hours. The formed compound may be purified by a purification method such as extraction, recrystallization, adsorption treatment, reprecipitation, column chromatography, or supercritical extraction.

[Production Method of Compound (3) in Which Y is (f)]

The amine body (f) can be obtained by adding acrylonitrile or the like to the hydroxyl group at the terminal of the multi-arm type polyethylene glycol derivative using an inorganic base such as sodium hydroxide or potassium hydroxide as a catalyst in a solvent such as water or acetonitrile to obtain a nitrile body and thereafter conducting a hydrogenation reaction of the nitrile group under a nickel or palladium catalyst in an autoclave. The use ratio of the inorganic base at the time of obtaining the nitrile body is not particularly limited but is preferably from 0.01 to 50% by mass, relative to the hydroxyl group at the terminal of the multi-arm type polyethylene glycol derivative. The use ratio of acrylonitrile is not particularly limited but is preferably molar equivalent or more, further preferably molar equivalent to 50 mol to the hydroxyl group at the terminal of the multi-arm type polyethylene glycol derivative. Moreover, acrylonitrile may be used as a solvent. The reaction temperature is preferably from −50 to 100° C., further preferably from −20 to 60° C. The reaction time is preferably from 10 minutes to 48 hours, further preferably from 30 minutes to 24 hours. The reaction solvent in the subsequent hydrogenation reaction of the nitrile body is not particularly limited so far as it is a solvent that does not participate in the reaction but is preferably toluene. The use ratio of the nickel or palladium catalyst is not particularly limited but is from 0.05 to 30% by mass, preferably from 0.5 to 20% by mass, relative to the nitrile body. The reaction temperature is preferably from 20 to 200° C., further preferably from 50 to 150° C. The reaction time is preferably from 10 minutes to 48 hours, further preferably from 30 minutes to 24 hours. Hydrogen pressure is preferably from 2 to 10 MPa, further preferably from 3 to 8 MPa. Moreover, in order to prevent dimerization, ammonia may be added into the reaction system. Ammonia pressure in the case of adding ammonia is not particularly limited but is from 0.1 to 10 MPa, further preferably from 0.3 to 2 MPa. The formed compound may be purified by a purification method such as extraction, recrystallization, adsorption treatment, reprecipitation, column chromatography, or supercritical extraction.

Alternatively, the amine body (f) can be also obtained by reacting the sulfonate body (m) with aqueous ammonia. The reaction is carried out in aqueous ammonia and the concentration of ammonia is not particularly limited but is preferably in the range of 10 to 40% by mass. The use ratio of aqueous ammonia is preferably from 1 to 300 times, relative to the mass of the sulfonate body (m). The reaction temperature is preferably from 0 to 100° C., further preferably from 20 to 80° C. The reaction time is preferably from 10 minutes to 72 hours, further preferably from 1 to 36 hours.

Moreover, the amine body (f) can be obtained by reacting the sulfonate body (m) with ammonia in an autoclave. The reaction solvent is not particularly limited but methanol and ethanol may be preferably mentioned. The amount of ammonia is preferably from 10 to 300% by mass, further preferably from 20 to 200% by mass, relative to the sulfonate body (m). The reaction temperature is preferably from 50 to 200° C., further preferably from 80 to 150° C. The reaction time is preferably from 10 minutes to 24 hours, further preferably from 30 minutes to 12 hours. The formed compound may be purified by the aforementioned purification method.

Furthermore, the amine body (f) can be also obtained by combining the hydroxyl group at the terminal of the multi-arm type polyethylene glycol derivative with phthalimide using the Mitsunobu reaction in an aprotic solvent, followed by deprotection with a primary amine. The reaction condition for the Mitsunobu reaction is not particularly limited but the reaction solvent is preferably chloroform or dichloromethane. The use ratio of triphenylphosphine and an azocarboxylic acid ester is not particularly limited but is preferably molar equivalent or more, further preferably molar equivalent to 50 mol to the hydroxyl group at the terminal of the multi-arm type polyethylene glycol derivative. The reaction temperature is preferably from 0 to 100° C., further preferably from 10 to 50° C. The reaction time is preferably from 10 minutes to 72 hours, further preferably from 30 minutes to 6 hours.

With regard to the deprotection, the primary amine to be used is not particularly limited but there may be preferably mentioned ammonia, methylamine, ethylamine, propylamine, butylamine, pentylamine, hexylamine, cyclohexylamine, ethanolamine, propanolamine, butanolamine, ethylenediamine, and the like. As a matter of course, these primary amines may be used as solvents. The use ratio of the primary amine is not particularly limited but it is preferably used in a ratio of molar equivalent or more, further preferably molar equivalent to 500 mol to the hydroxyl group at the terminal of the multi-arm type polyethylene glycol derivative. The reaction solvent is not particularly limited but methanol is preferred. The reaction temperature is preferably from 0 to 100° C., further preferably from 20 to 80° C. The reaction time is preferably from 10 minutes to 72 hours, further preferably from 1 to 10 hours. The formed compound may be purified by the aforementioned purification method.

[Production Method of Compound (3) in Which Y is (g)]

An oxyamine body (g) can be obtained by reacting the active carbonate body (c) or (d) with a compound (g1) represented by the following general formula in the presence of a base catalyst such as triethylemine or pyridine to convert the carbonate body into an oxyphthalimide body, followed by dephthalimidation in the presence of a primary amine. The reaction solvent for the oxyphthalimidation is not particularly limited so far as it is no solvent or a polar solvent but is preferably dimethylformamide. The use ratio of the base catalyst is not particularly limited but is preferably molar equivalent or more, further preferably in the range of molar equivalent to 20 mol to the active carbonate group. The use ratio of compound (g1) is preferably molar equivalent or more, further preferably molar equivalent to 20 mol to the active carbonate group. The reaction temperature is preferably from 0 to 100° C., further preferably from 20 to 80° C. The reaction time is preferably from 10 minutes to 48 hours, further preferably from 30 minutes to 12 hours. The formed compound may be purified by a purification method such as extraction, recrystallization, adsorption treatment, reprecipitation, column chromatography, or supercritical extraction or may be used in the subsequent step without purification.

The reaction solvent for the dephthalimidation is not particularly limited but methanol is preferred. The primary amine to be used is not particularly limited but there may be preferably mentioned ammonia, methylamine, ethylamine, propylamine, butylamine, pentylamine, hexylamine, cyclohexylamine, ethanolamine, propanol amine, butanolamine, ethylenediamine, and the like. As a matter of course, these primary amines may be used as solvents. The use ratio of the primary amine is not particularly limited but is preferably molar equivalent or more, further preferably in the range of molar equivalent to 50 mol to the active carbonate group. The reaction temperature is preferably from 0 to 100° C., further preferably from 20 to 80° C. The reaction time is preferably from 10 minutes to 48 hours, further preferably from 30 minutes to 12 hours. The formed compound may be purified by the aforementioned purification method.

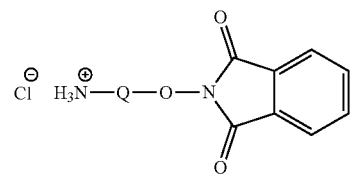

(g1)

wherein Q represents a linear alkylene group having 1 to 7 carbon atoms.

[Production Method of Compound (3) in Which Y is (n)]

A maleimide body (n) can be obtained by reacting the amine body (f) with maleic anhydride in an aforementioned aprotic solvent or no solvent to obtain a maleamide body and then subjecting it to a ring-closure reaction using acetic anhydride or sodium acetate as catalysts. The use ratio of maleic anhydride in the maleamidation reaction is not particularly limited but is preferably molar equivalent or more, further preferably molar equivalent to 5 mol to the amino group. The reaction temperature is preferably from 0 to 200° C., further preferably from 20 to 120° C. The reaction time is preferably from 10 minutes to 48 hours, further preferably from 30 minutes to 12 hours. The formed compound may be purified by a purification method such as extraction, recrystallization, adsorption treatment, reprecipitation, column chromatography, or supercritical extraction or may be used in the fsubsequent step without purification.

The reaction solvent for the subsequent ring-closure reaction is not particularly limited but an aprotic solvent or acetic anhydride is preferred. The use ratio of sodium acetate is not particularly limited but is preferably molar equivalent or more, further preferably molar equivalent to 50 mol to the maleamide group. The reaction temperature is preferably from 0 to 200° C., further preferably from 20 to 150° C. The reaction time is preferably from 10 minutes to 48 hours, further preferably from 30 minutes to 12 hours. The formed compound may be purified by the aforementioned purification method.

Moreover, the maleimide body (n) can be also obtained by reacting a compound (n1) represented by the following general formula with the amine body (f) in an aforementioned aprotic solvent or no solvent. The use ratio of (n1) is preferably molar equivalent or more, further preferably molar equivalent to 5 mol to the amino group (f). The reaction temperature is preferably from 0 to 200° C., further preferably from 20 to 80° C. The reaction time is preferably from 10 minutes to 48 hours, further preferably from 30 minutes to 12 hours. Light may be shielded at the time of the reaction. The formed compound may be purified by the aforementioned purification method.

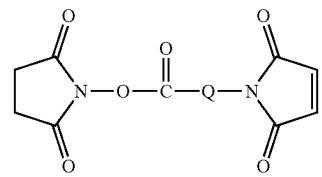

(n1)

wherein Q represents a linear alkylene group having 1 to 7 carbon atoms.

[Production Method of Compound (3) in Which Y is (e)]

An aldehyde body (e) can be obtained by reacting the sulfonate body (m) with a compound (e1) represented by the following general formula in an aforementioned aprotic solvent or in no solvent to obtain an acetal body and then subjecting it to hydrolysis under an acidic condition. The use ratio of (e1) is preferably molar equivalent or more, further preferably molar equivalent to 50 mol to the sulfonate group. (e1) can be prepared from a corresponding alcohol using metal sodium, metal potassium, sodium hydride, potassium hydride, sodium methoxide, potassium t-butoxide, or the like. The reaction temperature is preferably from 0 to 300° C., further preferably from 20 to 150° C. The reaction time is preferably from 10 minutes to 48 hours, further preferably from 30 minutes to 24 hours.

Moreover, in the case of using the compound (e2), the acetal body can be obtained by converting the hydroxyl group at the terminal of the multi-arm type polyethylene glycol derivative into an alcoholate by the aforementioned method and subsequently conducting reaction in an aprotic solvent or in no solvent using (e2) in a ratio of molar equivalent or more, preferably molar equivalent to 100 mol to the hydroxyl group at the terminal of the multi-arm type polyethylene glycol derivative. The reaction temperature is preferably from 0 to 300° C., further preferably from 20 to 150° C. The reaction time is preferably from 10 minutes to 48 hours, further preferably from 30 minutes to 24 hours.

Furthermore, in the case of using the compound (e3), the acetal body can be obtained by reacting the carboxyl body (a), the succinimide body (b), or the active carbonate body (c) or (d) with (e3). In the reaction with (e3), the solvent is not particularly limited but the reaction is preferably conducted in an aprotic solvent. The use ratio of (e3) is preferably molar equivalent or more, further preferably molar equivalent to 10 mol to the carboxyl group, the succinimide group, or the active carbonate group. The reaction temperature is preferably from −30 to 200° C., further preferably from 0 to 150° C. The reaction time is preferably from 10 minutes to 48 hours, further preferably from 30 minutes to 24 hours. In the case of using the carboxyl body (a), a condensing agent such as DCC or EDC may be appropriately used. The formed compound may be purified by a purification method such as extraction, recrystallization, adsorption treatment, reprecipitation, column chromatography, or supercritical extraction or may be used in the subsequent step without purification.

The subsequent aldehyde formation reaction can be achieved by transforming the acetal body into a 0.1 to 50% aqueous solution and hydrolyzing it in an aqueous solution which is adjusted to pH 1 to 4 with an acid such as acetic acid, phosphoric acid, sulfuric acid, or hydrochloric acid. The reaction temperature is preferably from −20 to 100° C., further preferably from 0 to 80° C. The reaction time is preferably from 10 minutes to 24 hours, further preferably from 30 minutes to 10 hours. The reaction may be conducted with shielding light. The formed compound may be purified by the aforementioned purification method.

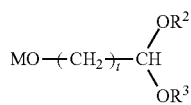

(e1)

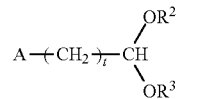

(e2)

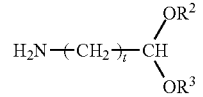

(e3)

wherein $R^2$ and $R^3$ are each a hydrocarbon group having 1 to 3 carbon atoms and may be the same or different from each other, and they may form a ring each other; M is sodium or potassium; A is a halogen atom selected from chlorine, bromine, and iodine or a sulfone-based protective group; and t is an integer of 1 to 12.

[Production Method of Compound (3) in Which Y is (k)]

A mercapto body (k) can be obtained by reacting the sulfonate body (m) with a thiation agent such as thiourea to form a thiazolium salt and then subjecting it to hydrolysis under an alkaline condition. The thiation reaction is conducted in acetonitrile or an alcohol solvent such as methanol, ethanol, or 2-propanol or in no solvent. The use ratio of the thiation agent is preferably molar equivalent or more, further preferably in the range of molar equivalent to 50 mol to the sulfonate group. The reaction temperature is preferably from 0 to 300° C., further preferably from 20 to 150° C. The reaction time is preferably from 10 minutes to 48 hours, further preferably from 30 minutes to 24 hours. The subsequent hydrolysis can be achieved by forming a 0.1 to 50% aqueous solution of the thiazolium salt body and hydrolyzing it in an aqueous solution which is adjusted to pH 10 to 14 with an alkali such as sodium hydroxide, potassium hydroxide, or potassium carbonate. The reaction temperature is preferably from −20 to 100° C., further preferably from 0 to 80° C. The reaction time is preferably from 10 minutes to 24 hours, further preferably from 30 minutes to 10 hours. The reaction may be conducted with shielding light. The formed compound may be purified by a purification method such as extraction, recrystallization, adsorption treatment, reprecipitation, column chromatography or supercritical extraction.

Moreover, the mercapto body (k) may be also obtained by reacting the sulfonate body (m) with a compound (k1) represented by the following general formula in an aforementioned aprotic solvent or in no solvent, followed by decomposition with a primary amine. The use ratio of (k1) is preferably molar equivalent or more, further preferably in the range of molar equivalent to 50 mol to the sulfonate group. The reaction temperature is preferably from 0 to 300° C., further preferably from 20 to 80° C. The reaction time is preferably from 10 minutes to 48 hours, further preferably from 30 minutes to 24 hours. The subsequent alkali decomposition with a primary amine is conducted in an aprotic solvent or in no solvent. The primary amine to be used is not particularly limited but there may be preferably mentioned ammonia, methylamine, ethylamine, propyl amine, butylamine, pentylamine, hexylamine, cyclohexylamine, ethanolamine, propanolamine, butanolamine, ethylenediamine, and the like. As a matter of course, these primary amines may be used as solvents. The formed compound may be purified by the aforementioned purification method.

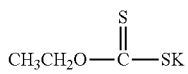

[Production Method of Compound (3) in Which Y is (l)]

A dipyridyl disulfide body (l) can be obtained by reacting the mercapto body (k) with 2,2-dipyridyl disulfide. The reaction solvent is not particularly limited but the reaction is preferably conducted in an alcohol solvent such as methanol, ethanol, or 2-propanol. The use ratio of 2,2-dipyridyl disulfide is preferably molar equivalent or more, further preferably molar equivalent to 50 mol to the mercapto group. The reaction temperature is preferably from −30 to 100° C., further preferably from 0 to 60° C. The reaction time is preferably from 10 minutes to 48 hours, further preferably from 30 minutes to 24 hours. The formed compound may be purified by a purification method such as extraction, recrystallization, adsorption treatment, reprecipitation, column chromatography, or supercritical extraction.

[Production Method of Compound (3) in Which Y is (p)]

An iodoacetyl body (p) can be obtained by reacting the amino body (f) with iodoacetic anhydride in an aforementioned aprotic solvent or no solvent. The use ratio of iodoacetic anhydride is not particularly limited but is preferably molar equivalent or more, further preferably molar equivalent to 5 mol to the amino group. The reaction temperature is preferably from 0 to 200° C., further preferably from 20 to 120° C. The reaction time is preferably from 10 minutes to 48 hours, further preferably from 30 minutes to 12 hours. The formed compound may be purified by a purification method such as extraction, recrystallization, adsorption treatment, reprecipitation, column chromatography, or supercritical extraction.

Moreover, the iodoacetyl body (p) can be also obtained by reacting the amino body (f) with iodoacetic acid in the presence of a condensing agent such as DCC or EDC in an aforementioned aprotic solvent or in no solvent. The condensing agent is not particularly limited but is preferably DCC. The use ratio of DCC is preferably molar equivalent or more, further preferably molar equivalent to 5 mol to the amino group. The use ratio of iodoacetic acid is not particularly limited but is preferably molar equivalent or more, further preferably molar equivalent to 5 mol to the amino group. The reaction temperature is preferably from 0 to 100° C., further preferably from 20 to 80° C. The reaction time is preferably from 10 minutes to 48 hours, further preferably from 30 minutes to 12 hours. The formed compound may be purified by the aforementioned purification method.

[Production Method of Compound (3) in Which Y is (h)]

A hydrazide body (h) can be obtained by reacting the succinimide body (b) or the active carbonate body (c) or (d) with t-butyl carbazate in an aforementioned aprotic solvent or no solvent, followed by deprotection of the t-butylcarbonyl group. The use ratio of t-butyl carbazate is not particularly limited but is preferably molar equivalent or more, further preferably molar equivalent to 10 mol to the succinimide group or the active carbonate group. The reaction temperature is preferably from 0 to 200° C., further preferably from 20 to 80° C. The reaction time is preferably from 10 minutes to 48 hours, further preferably from 30 minutes to 12 hours. The formed compound may be purified by a purification method such as extraction, recrystallization, adsorption treatment, reprecipitation, column chromatography, or supercritical extraction.

[Production Method of Compound (3) in Which Y is (j)]

An acetylene body (j) can be obtained by reacting the succinimide body (b) or the active carbonate body (c) or (d) with a compound (j 1) represented by the following general formula in an aforementioned aprotic solvent or no solvent. The use ratio of (j 1) is not particularly limited but is preferably molar equivalent or more, further preferably molar equivalent to 50 mol of (j 1) to the succinimide group or the active carbonate group. The reaction temperature is preferably from 0 to 300° C., further preferably from 20 to 150° C. The reaction time is preferably from 10 minutes to 48 hours, further preferably from 30 minutes to 24 hours. The formed compound may be purified by a purification method such as extraction, recrystallization, adsorption treatment, reprecipitation, column chromatography, or supercritical extraction.

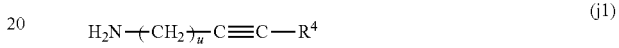

wherein u is an integer of 1 to 5; and $R^4$ represents a hydrogen atom or a hydrocarbon group having 1 to 5 carbon atoms.

[Production Method of Compound (3) in Which Y is (i)]

An azide body (i) can be obtained by reacting the sulfonate body (m) with sodium azide in an aforementioned aprotic solvent or in no solvent. The use ratio of sodium azide is preferably molar equivalent or more, further preferably molar equivalent to 50 mol to the sulfonate group. The reaction temperature is preferably from 0 to 300° C., further preferably from 20 to 150° C. The reaction time is preferably from 10 minutes to 48 hours, further preferably from 30 minutes to 24 hours. The formed compound may be purified by a purification method such as extraction, recrystallization, adsorption treatment, reprecipitation, column chromatography, or supercritical extraction.

According to the invention, a highly pure multi-arm type polyethylene glycol derivative (1) can be industrially produced more efficiently than the case of conventional production methods.

EXAMPLES

The following further specifically describe the present invention based on Examples but the invention should not be construed as being limited thereto. Incidentally, $^1$H-NMR and GPC were used for analysis and identification of compounds in the examples.

<Analytical Method on $^1$H-NMR>

For $^1$H-NMR analysis, JNM-ECP400 manufactured by JOEL Ltd. was used. Integrated values in NMR measurement values are theoretical values.

<Analytical Method on GPC>

For GPC analysis, measurement was conducted with a system using any of DMF or water as an eluent. Measurement conditions for each system are shown below.

Case of DMF System

Apparatus: SHIMADZU LC-10Avp

Column: PL gel MIXED-D×2 (Polymer Laboratory)

Developing solvent: dimethylformamide

Flow rate: 0.7 ml/min

Column temperature: 65° C.

Detector: RI

Sample amount: 1 mg/g, 100 μl

Case of Water System

Apparatus: alliance (Waters)
Column: ultrahydrogel 500+ultrahydrogel 250 (Waters)
Developing solvent: 100 mM sodium acetate, 0.02% $NaN_3$ buffer solution (pH 5.2)
Flow rate: 0.5 ml/min
Column temperature: 30° C.
Detector: RI
Sample amount: 5 mg/g, 20 µl The GPC measurement value is an analysis value at a main peak with removing high-molecular-weight impurities and low-molecular-weight impurities by vertically cutting the baseline from inflection points of an elution curve. Fraction % represents a ratio of the main peak from the elution start point to the elution final point relative to the whole peak, $M_n$ represents number-average molecular weight, $M_w$ represents weight-average molecular weight, $M_p$ represents peak top molecular weight, and Mw/Mn represents polydispersity.

<Molecular Weight Measurement on TOF-MS>

Measurement was conducted using TOF-MS (manufactured by Bruker, autoflex III) using Dithranol as a matrix and sodium trifluoroacetate as a salt. For analysis, FlexAnalysis was used and analysis of molecular weight distribution was conducted on Polytools. The obtained value at gravity center was described as a value of molecular weight.

<Molecular Weight Measurement by Hydroxyl Value Measurement>

According to JIS K1557-1, the hydroxyl value was measured by A method (acetic anhydride/pyridine). The molecular weight was calculated from the measured hydroxyl value according to the following equation.

(Molecular Weight)=56.1×1,000×8/(Hydroxyl Value)

Example 1

Synthesis of Compounds (I), (II), (III), and (IV) (Cases where L=n-Butylene Group, k=1, Molecular Weight: about 5,000, 10,000, 20,000, and 40,000)

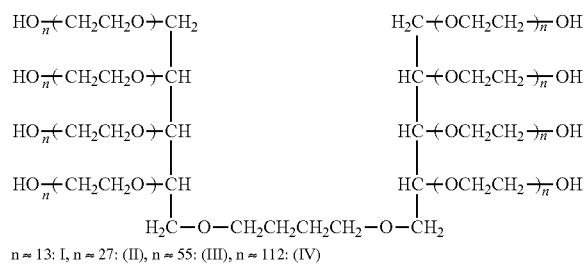

n ≈ 13: I, n ≈ 27: (II), n ≈ 55: (III), n ≈ 112: (IV)

Example 1-1

Synthesis of 2,3,4,5-Dibenzylidenexylitol

Into a reactor fitted with a thermometer, a nitrogen-inlet tube and a stirrer were placed 150 g of xylitol and 3,700 g of 6M sulfuric acid, and xylitol was dissolved at room temperature. After 315 g of benzaldehyde was added thereto, the mixture was heated to about 30° C., and stirring was continued to precipitate crystals. The mixture was stirred as it was for 6 hours or more. Then, 4.5 L of cooled distilled water was added, the precipitate was collected by filtration, the crystals were suspended in 3 L of an aqueous ethanol solution, and neutralization was performed by adding a 10 N aqueous sodium hydroxide solution, followed by filtration. The obtained crystals were further subjected to suspension washing with an aqueous ethanol solution, a mixed solution of ethanol/methyl t-butyl ether (MTBE), and MTBE in the order and filtration, repeatedly. Then, drying was performed under reduced pressure to obtain 260 g of 2,3,4,5-dibenzylidenexylitol.

$^1$H-NMR (CDCl$_3$, internal standard: TMS) δ (ppm):
3.80-4.40 (7H, m, —C$\underline{H}_2$—O—, —C$\underline{H}$—O—),
5.59 (1H, s, Ph—C$\underline{H}$—O—),
5.67 (1H, s, Ph—C$\underline{H}$—O—),
7.30-7.65 (10H, m, $\underline{Ph}$—CH—O—)

Example 1-2

Synthesis of 1,1'-Butylene-bis(2,3,4,5-dibenzylidenexylitol)

To a 5,000 ml round-bottom flask fitted with a thermometer, a nitrogen-inlet tube and a stirrer were added 266 g (0.81 mol) of 2,3,4,5-dibenzylidenexylitol, 2,400 g of dimethylformamide (DMF) and 1,600 g of toluene were added, and dissolution was achieved under a nitrogen atmosphere. Then, azeotropic dehydration was performed at 110 to 120° C. After the azeotropic dehydration, the mixture was cooled, 94.8 g (0.84 mol) of potassium t-butoxide was added, and the mixture was stirred at 30 to 40° C. for 30 minutes. On the other hand, 80 g (0.33 mol) of 1,4-butanediol dimethanesulfonate was dissolved in 660 g of dehydrated DMF, and then the resultant solution was added dropwise to the reaction solution under stirring at 30 to 40° C. over a period of 30 minutes. After completion of the dropwise addition, the temperature was raised to 50° C. and the reaction was performed for 2 hours. After completion of the reaction, the reaction solution was cooled to 10° C. or lower and stirred for 30 minutes to precipitate crystals, and the mixture was stirred as it was for 1 hour. The precipitate was collected by filtration, the crystals were suspended in 2.5 L of an aqueous ethanol solution, and suspension washing and filtration were repeated 3 times. Next, 4,800 g of DMF was added and recrystallization was perform. The obtained crystals were further added with 2,560 g of methyl t-butyl ether (MTBE), and suspension washing and filtration were repeated twice, followed by drying under reduced pressure to obtain 150 g of 1,1'-butylene-bis(2,3,4,5-dibenzylidenexylitol).

$^1$H-NMR (CDCl$_3$, internal standard: TMS) δ (ppm):
1.61 (4H, quint, —OCH$_2$C$\underline{H}_2$C$\underline{H}_2$CH$_2$—O—),
3.44-4.38 (18H, m, —OC$\underline{H}_2$CH$_2$CH$_2$C$\underline{H}_2$—O—, —C$\underline{H}_2$—O—, —C$\underline{H}$—O—),
5.57 (2H, s, Ph—C$\underline{H}$—O—),
5.63 (2H, s, Ph—C$\underline{H}$—O—),
7.30-7.65 (20H, m, $\underline{Ph}$—CH—O—)

Example 1-3

Synthesis of 1,1'-Butylene-bisxylitol

To a 3,000 ml round-bottom flask fitted with a thermometer, a nitrogen-inlet tube, and a stirrer were added 290 g (0.41 mol) of 1,1'-butylene bis(2,3,4,5-dibenzylidenexylitol), 870 g of trifluoroacetic acid (TFA) and 290 g of ion-exchanged water, and the mixture was heated to 50° C. and stirred for 4 hours. The mixture was cooled to 30° C. or lower, 1,450 g of toluene was added, and the resultant was stirred for 30 minutes or more. After the stirring was stopped, the layers were separated, the toluene layer was removed, 1,450 g of toluene was added to the aqueous layer, and liquid separation and washing were performed again. This liquid separation operation was repeated 7 times in total. Next, after TFA was concentrated and distilled off under reduced pressure, 1,450 g of ethanol was added, and azeotropic dehydration was repeated 3 times. After 870 g of methanol was added to the concentrated solution and homogenization was performed, Kyoward 1000 (manufactured by Kyowa Chemical Industry Co., Ltd.) was added, and after stirring for 30 minutes, the mixture was filtrated. An ion exchange resin (SMN-1, manufactured by Mitsubishi Chemical Corporation) was added to the filtrate, and the mixture was stirred for 30 minutes and then filtrated. The filtrate was concentrated to obtain 126 g of 1,1'-butylene-bisxylitol (V) having the following structure.

$^1$H-NMR (D$_2$O, internal standard: TMS) δ (ppm):
1.66 (4H, quint, —OCH$_2$C$\underline{H_2}$C$\underline{H_2}$CH$_2$—O—),
3.56-3.75 (14H, m, —OC$\underline{H_2}$CH$_2$CH$_2$C$\underline{H_2}$—O—, —C$\underline{H_2}$—O—, —C$\underline{H}$—O—),
3.79-3.82 (2H, m, —C$\underline{H}$—O—),
3.91-3.93 (2H, m, —C$\underline{H}$—O—)

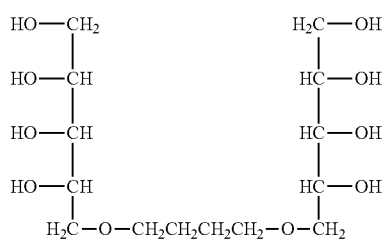

(V)

Example 1-4

Synthesis of Compound (I) (Case of Molecular Weight of 5,000)

Sixty grams of 1,1'-butylene-bisxylitol (V) obtained in Example 1-3 was warmed and, while washing it with 41 g of methanol, was charged into a 5 L autoclave. Subsequently, 5.8 g of potassium hydroxide and 12 g of ion-exchanged water were added to a 50 ml beaker to prepare an aqueous potassium hydroxide solution, which was then charged into the 5 L autoclave. Then, 600 g of dehydrated toluene was added thereto and an azeotropic dehydration operation was repeated three times at 80° C., under slightly reduced pressure. After the azeotropic dehydration, 1,594 g of dehydrated toluene was added and, after the inside of the system was replaced by nitrogen, 740 g (16.8 mol) of ethylene oxide was added at 80 to 150° C. under a pressure of 1 MPa or less, followed by continuation of the reaction for another 1 hour. After the reaction, the whole was cooled to 60° C., 604 g of the reaction solution was taken out of the autoclave, and pH was adjusted to 7.5 with an 85% aqueous phosphoric acid solution to obtain the following compound (I).

$^1$H-NMR (CDCl$_3$, internal standard: TMS) δ (ppm):
1.57 (4H, br, —OCH$_2$C$\underline{H_2}$C$\underline{H_2}$CH$_2$—O—),
2.66 (8H, br, —O$\underline{H}$),
3.40 (4H, br, —OC$\underline{H_2}$CH$_2$CH$_2$CH$_2$—O—),
3.50-3.81 (430H, m, —C$\underline{H_2}$O(C$\underline{H_2}$C$\underline{H_2}$O)$_n$H, CHO(C$\underline{H_2}$C$\underline{H_2}$O)$_n$H, —C$\underline{H_2}$—OCH$_2$C$\underline{H_2}$C$\underline{H_2}$CH$_2$O—C$\underline{H_2}$—)

GPC analysis (DMF system):
main fraction: 99.5%,
Mn: 3,838, Mw: 3,905, Mw/Mn: 1.017, Mp: 3,903

Molecular weight (TOF-MS); 4,974
Molecular weight (hydroxyl value); 5,026

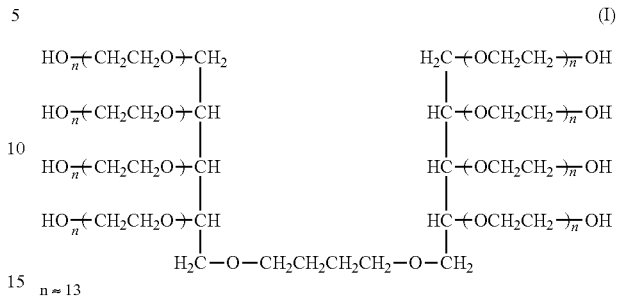

(I)

n ≈ 13

Example 1-5

Synthesis of Compound (II) (Case of Molecular Weight of 10,000)

To about 1,764 g of the reaction solution remaining in the reaction vessel in Example 1-4 was added 615 g (14.0 mol) of ethylene oxide at 80 to 150° C. under a pressure of 1 MPa or less, followed by continuation of the reaction for another 1 hour. After the reaction, the whole was cooled to 60° C., 1,529 g of the reaction solution was taken out of the vessel, pH was adjusted to 7.5 with an 85% aqueous phosphoric acid solution, and toluene was removed by distillation to obtain the following compound (II).

$^1$H-NMR (CDCl$_3$, internal standard: TMS) δ (ppm):
1.57 (4H, br, —OCH$_2$C$\underline{H_2}$C$\underline{H_2}$CH$_2$—O—),
2.365 (8H, br, —O$\underline{H}$),
3.40 (4H, s, —OC$\underline{H_2}$CH$_2$CH$_2$CH$_2$—O—),
3.50-3.81 (878H, m, —C$\underline{H_2}$O(C$\underline{H_2}$C$\underline{H_2}$O)$_n$H, CHO(C$\underline{H_2}$C$\underline{H_2}$O)$_n$H, —C$\underline{H_2}$—OCH$_2$C$\underline{H_2}$C$\underline{H_2}$CH$_2$O—C$\underline{H_2}$—)

GPC analysis (DMF system):
main fraction: 99.0%,
Mn: 7,123, Mw: 7,262, Mw/Mn: 1.019, Mp: 7,282
Molecular weight (TOF-MS); 10,418
Molecular weight (hydroxyl value); 9,968

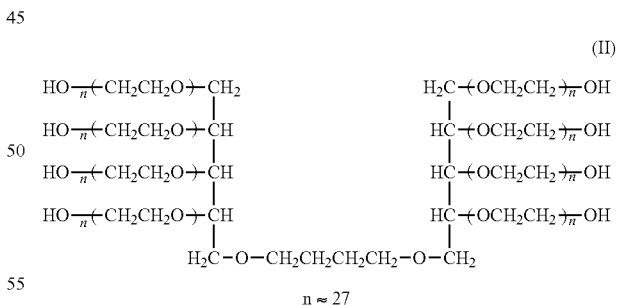

(II)

n ≈ 27

Example 1-6

Synthesis of Compound (III) (Case of Molecular Weight of 20,000)

To about 809 g of the reaction solution remaining in the reaction vessel in Example 1-5 was added 390 g (8.85 mol) of ethylene oxide at 80 to 150° C. under a pressure of 1 MPa or less, followed by continuation of the reaction for another 1 hour. After the reaction, the whole was cooled to 60° C., 978 g of the reaction solution was taken out of the vessel, pH was adjusted to 7.5 with an 85% aqueous phosphoric acid solution, and toluene was removed by distillation to obtain the following compound (III).

$^1$H-NMR (CDCl$_3$, internal standard: TMS) δ (ppm):
1.57 (4H, br, —OCH$_2$C$\underline{H}_2$C$\underline{H}_2$CH$_2$—O—),
2.57 (8H, br, —O$\underline{H}$),
3.40 (4H, s, —OC$\underline{H}_2$CH$_2$CH$_2$C$\underline{H}_2$—O—),
3.50-3.81 (1774H, m, —C$\underline{H}_2$O(C$\underline{H}_2$C$\underline{H}_2$O)$_n$H, C$\underline{H}$O (C$\underline{H}_2$C$\underline{H}_2$O)$_n$H, —C$\underline{H}_2$—OCH$_2$CH$_2$CH$_2$O—C$\underline{H}_2$—)

GPC analysis (DMF system):
  main fraction: 98.4%,
  Mn: 14,140, Mw: 14,499, Mw/Mn: 1.025, Mp: 14,910
Molecular weight (TOF-MS); 20,233
Molecular weight (hydroxyl value); 19,858

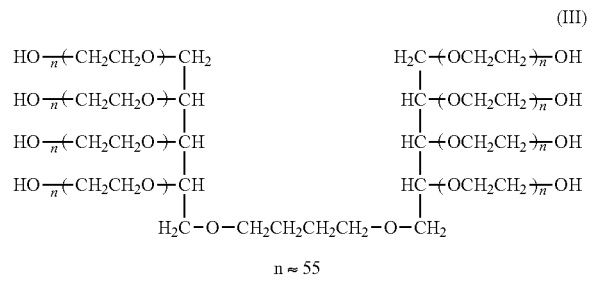

n ≈ 55

(III)

Example 1-7

Synthesis of Compound (IV) (Case of Molecular Weight of 40,000)

To about 199 g of the reaction solution remaining in the reaction vessel in Example 1-6 was added 103 g (2.34 mol) of ethylene oxide at 80 to 150° C. under a pressure of 1 MPa or less, followed by continuation of the reaction for another 1 hour. After the reaction, the whole was cooled to 60° C., all the amount of the reaction solution was taken out of the vessel, pH was adjusted to 7.5 with an 85% aqueous phosphoric acid solution, and toluene was removed by distillation to obtain the following compound (IV).

$^1$H-NMR (CDCl$_3$, internal standard: TMS) δ (ppm):
1.57 (4H, br, —OCH$_2$C$\underline{H}_2$C$\underline{H}_2$CH$_2$—O—),
2.589 (8H, br, —O$\underline{H}$),
3.40 (4H, s, —OC$\underline{H}_2$CH$_2$CH$_2$C$\underline{H}_2$—O—), 3.50-3.81 (3598H, m, —C$\underline{H}_2$O(C$\underline{H}_2$C$\underline{H}_2$O)$_n$H, C$\underline{H}$O(C$\underline{H}_2$C$\underline{H}_2$O)$_n$H, —C$\underline{H}_2$—OCH$_2$CH$_2$CH$_2$O—C$\underline{H}_2$—)

GPC analysis (DMF system):
  main fraction: 96.6%,
  Mn: 27,158, Mw: 27,691, Mw/Mn: 1.020, Mp: 27,945
Molecular weight (TOF-MS); 40,071
Molecular weight (hydroxyl value); 39,932

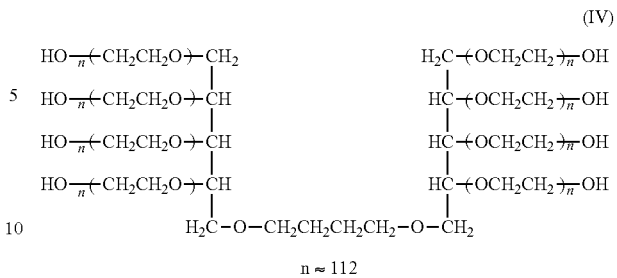

n ≈ 112

(IV)

Example 2-1

Synthesis of Cyanoethyl Body (Case of Molecular Weight of About 10,000)

To a 500 ml round-bottom flask fitted with a thermometer, a nitrogen-inlet tube, a stirrer, and a cooling tube were added 50 g (5 mmol) of the compound (II) obtained in the above Example 1-5 and 50 g of ion-exchanged water, and the whole was heated to 40° C. to achieve dissolution. After the dissolution, the whole was cooled to 10° C. or lower and 5 g of a 50% aqueous potassium hydroxide solution was added thereto. Subsequently, while the temperature was kept at 5 to 10° C., 42.5 g (800 mmol) of acrylonitrile was added dropwise over a period of 2 hours. After completion of the dropwise addition, the reaction was further conducted for 4 hours and, after 50 g of ion-exchanged water was added, neutralization was achieved by adding 3 g of an 85% aqueous phosphoric acid solution. After 75 g of ethyl acetate was added and the whole was stirred, it was allowed to stand and an upper ethyl acetate layer was discarded. The extraction with ethyl acetate was repeated nine times. After completion of the extraction, extraction with 250 g of chloroform was performed. The resulting chloroform layer was dried over 25 g of magnesium sulfate and, after filtration, was concentrated. The concentrated liquid was dissolved with adding 150 g of ethyl acetate, and hexane was added until crystals were precipitated. The crystals were collected by filtration and again dissolved in 150 g of ethyl acetate and, after cooling to room temperature, hexane was added until crystals were precipitated. The crystals were collected by filtration and dried to obtain the following cyanoethyl body (VI).

$^1$H-NMR (CDCl$_3$, internal standard: TMS) δ (ppm):
1.57 (4H, br, —OCH$_2$C$\underline{H}_2$C$\underline{H}_2$CH$_2$—O—),
2.63 (16H, t, —C$\underline{H}_2$CH$_2$CN),
3.39 (4H, br, —OC$\underline{H}_2$CH$_2$CH$_2$C$\underline{H}_2$—O—),
3.50-3.80 (894H, m, —C$\underline{H}_2$O(C$\underline{H}_2$C$\underline{H}_2$O)$_n$H, C$\underline{H}$O (C$\underline{H}_2$C$\underline{H}_2$O)$_n$H, —C$\underline{H}_2$—OCH$_2$CH$_2$CH$_2$O—C$\underline{H}_2$—, —C$\underline{H}_2$CH$_2$CN)

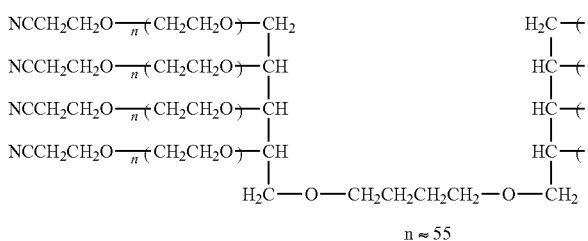 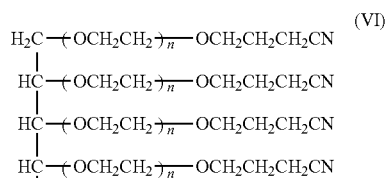

(VI)

n ≈ 55

Example 2-2

Synthesis of Propylamino Body (Case of Molecular Weight of About 10,000)

To a 1 L autoclave, 46 g of the cyanoethyl body, i.e, the compound (VI) obtained in the above Example 2-1 were added 533 g of toluene and 4.1 g of nickel (5136p manufactured by N. E. MCAT Company), and the whole was heated to 60° C. Pressurization was performed with ammonia until inner pressure reached 1 MPa and thereafter, hydrogen was introduced to achieve pressurization until the inner pressure reached 4.5 MPa, followed by reaction at 130° C. for 3 hours. After the reaction, the reaction solution was cooled to 80° C. and purging with nitrogen was repeated until ammonia odor disappeared. All the amount of the reaction solution was taken out and filtrated. After the filtrate was cooled to room temperature, hexane was added until crystals were precipitated. The crystals were collected by filtration and dried to obtain the following amine body (VII).
$^1$H-NMR (CDCl$_3$, internal standard: TMS) δ (ppm):
1.57 (4H, br, —OCH$_2$C$\underline{H}_2$C$\underline{H}_2$CH$_2$—O—),
1.72 (16H, quint, —CH$_2$C$\underline{H}_2$CH$_2$NH$_2$),
2.79 (16H, t, —CH$_2$CH$_2$C$\underline{H}_2$NH$_2$),
3.39 (4H, br, —OC$\underline{H}_2$CH$_2$CH$_2$C$\underline{H}_2$—O—),
3.50-3.80 (894H, m, —C$\underline{H}_2$O(C$\underline{H}_2$C$\underline{H}_2$O)$_n$H, C$\underline{H}_2$O (C$\underline{H}_2$C$\underline{H}_2$O)$_n$H, —C$\underline{H}_2$—OC$\underline{H}_2$CH$_2$CH$_2$C$\underline{H}_2$O—C$\underline{H}_2$—, —C$\underline{H}_2$CH$_2$CH$_2$NH$_2$)
GPC analysis (water system):
    main fraction: 96.9%,
    Mn: 6,781, Mw: 6,896, Mw/Mn: 1.017, Mp: 6,874

Example 3-1

Synthesis of Cyanoethyl Body (Case of Molecular Weight of About 20,000)

To a 500 ml round-bottom flask fitted with a thermometer, a nitrogen-inlet tube, a stirrer, and a cooling tube were added 50 g (2.5 mmol) of the compound (III) obtained in the above Example 1-6 and 50 g of ion-exchanged water, and the whole was heated to 40° C. to achieve dissolution. After the dissolution, the whole was cooled to 10° C. or lower and 5 g of a 50% aqueous potassium hydroxide solution was added thereto. Subsequently, while the temperature was kept at 5 to 10° C., 21.2 g (400 mmol) of acrylonitrile was added dropwise over a period of 2 hours. After completion of the dropwise addition, the reaction was further conducted for 4 hours and, after 50 g of ion-exchanged water was added, neutralization was achieved by adding 3 g of an 85% aqueous phosphoric acid solution dropwise. After 75 g of ethyl acetate was added and the whole was stirred, it was allowed to stand and an upper ethyl acetate layer was discarded. The extraction with ethyl acetate was repeated nine times. After completion of the extraction, extraction with 250 g of chloroform was performed. The resulting chloroform layer was dried over 15 g of magnesium sulfate and, after filtration, was concentrated. The concentrated liquid was dissolved with adding 150 g of ethyl acetate, and hexane was added until crystals were precipitated. The crystals were collected by filtration and again dissolved in 150 g of ethyl acetate under heating and, after cooling to

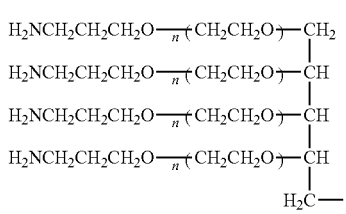 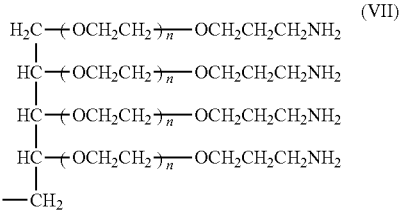

(VII)

n ≈ 27 room temperature, hexane was added until crystals were precipitated. The crystals were collected by filtration and dried to obtain the following cyanoethyl body (VIII).
$^1$H-NMR (CDCl$_3$, internal standard: TMS) δ (ppm):
1.57 (4H, br, —OCH$_2$C$\underline{H}_2$C$\underline{H}_2$CH$_2$—O—),
2.63 (16H, t, —C$\underline{H}_2$CH$_2$CN),
3.39 (4H, br, —OC$\underline{H}_2$CH$_2$CH$_2$C$\underline{H}_2$—O—),
3.50-3.80 (1790H, m, —C$\underline{H}_2$O(C$\underline{H}_2$C$\underline{H}_2$O)$_n$H, C$\underline{H}$O (C$\underline{H}_2$C$\underline{H}_2$O)$_n$H, —C$\underline{H}_2$—OC$\underline{H}_2$CH$_2$C$\underline{H}_2$CH$_2$O—C$\underline{H}_2$—, —C$\underline{H}_2$CH$_2$CN)

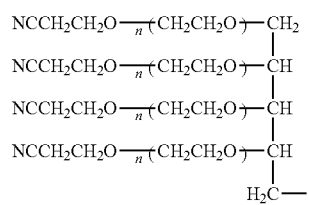
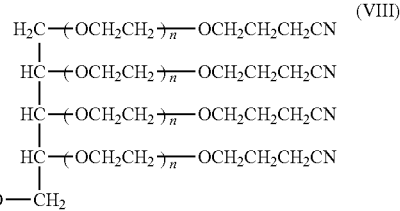

(VIII)

n ≈ 55

Example 3-2

Synthesis of Propylamino Body (Case of Molecular Weight of About 20,000)

To a 1 L autoclave were added 20 g of the cyanoethyl body, i.e, the compound (VIII) obtained in the above Example 3-1, 555 g of toluene, and 1.8 g of nickel (5136p manufactured by N. E. MCAT Company), and the whole was heated to 60° C. Pressurization was performed with ammonia until inner pressure reached 1 MPa and thereafter, hydrogen was introduced to achieve pressurization until the inner pressure reached 4.5 MPa, followed by reaction at 130° C. for 3 hours. After the reaction, the reaction solution was cooled to 80° C. and purging with nitrogen was repeated until ammonia odor disappeared. All the amount of the reaction solution was taken out and filtrated. After the filtrate was cooled to room temperature, hexane was added until crystals were precipitated. The crystals were collected by filtration and dried to obtain the following amine body (IX).
$^1$H-NMR (CDCl$_3$, internal standard: TMS) δ (ppm):
1.57 (4H, br, —OCH$_2$C$\underline{H}_2$C$\underline{H}_2$CH$_2$—O—),
1.72 (16H, quint, —CH$_2$C$\underline{H}_2$CH$_2$NH$_2$),
2.79 (16H, t, —CH$_2$CH$_2$C$\underline{H}_2$NH$_2$),
3.39 (4H, br, —OC$\underline{H}_2$CH$_2$CH$_2$C$\underline{H}_2$—O—),
3.50-3.80 (1790H, m, —C$\underline{H}_2$O(C$\underline{H}_2$C$\underline{H}_2$O)$_n$H, C$\underline{H}$O (C$\underline{H}_2$C$\underline{H}_2$O)$_n$H, —C$\underline{H}_2$—OC$\underline{H}_2$CH$_2$C$\underline{H}_2$CH$_2$O—C$\underline{H}_2$—, —C$\underline{H}_2$CH$_2$CH$_2$NH$_2$)
GPC analysis (water system):
  main fraction: 97.5%,
  Mn: 13,844, Mw: 14,133, Mw/Mn: 1.021, Mp: 14,203

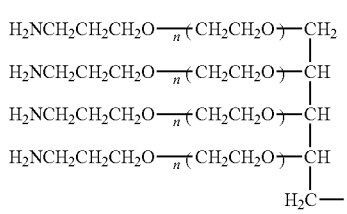
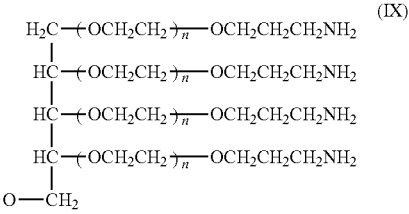

(IX)

n ≈ 55

Example 4-1

Synthesis of Cyanoethyl Body (Case of Molecular Weight of About 40,000)

To a 500 ml round-bottom flask fitted with a thermometer, a nitrogen-inlet tube, a stirrer, and a cooling tube were added 50 g (1.25 mmol) of the compound (IV) obtained in the above Example 1-7 and 50 g of ion-exchanged water, and the whole was heated to 40° C. to achieve dissolution. After the dissolution, the whole was cooled to 10° C. or lower and 5 g of a 50% aqueous potassium hydroxide solution was added thereto. Subsequently, while the temperature was kept at 5 to 10° C., 26.5 g (499 mmol) of acrylonitrile was added dropwise over a period of 2 hours. After completion of the dropwise addition, the reaction was further conducted for 4 hours and, after 50 g of ion-exchanged water was added, neutralization was achieved by adding 3 g of an 85% aqueous phosphoric acid solution. After 75 g of ethyl acetate was added and the whole was stirred, it was allowed to stand and an upper ethyl acetate layer was discarded. The extraction with ethyl acetate was repeated nine times. After completion of the extraction, extraction with 250 g of chloroform was performed. The resulting chloroform layer was dried over 15 g of magnesium sulfate and, after filtration, was concentrated. The concentrated liquid was dissolved with adding 150 g of ethyl acetate, and hexane was added until crystals were precipitated. The crystals were collected by filtration and again dissolved in 150 g of ethyl acetate under heating and, after cooling to room temperature, hexane was added until crystals were precipitated. The crystals were collected by filtration and dried to obtain the following cyanoethyl body (X).

$^1$H-NMR (CDCl$_3$, internal standard: TMS) δ (ppm):
1.57 (4H, br, —OCH$_2$C$\underline{H}_2$C$\underline{H}_2$CH$_2$—O—),
2.63 (16H, t, —CH$_2$C$\underline{H}_2$CN),
3.39 (4H, br, —OC$\underline{H}_2$CH$_2$CH$_2$C$\underline{H}_2$—O—),
3.50-3.80 (3614H, m, —C$\underline{H}_2$O(C$\underline{H}_2$C$\underline{H}_2$O)$_n$H, C$\underline{H}$O(C$\underline{H}_2$C$\underline{H}_2$O)$_n$H, —C$\underline{H}_2$—OCH$_2$CH$_2$CH$_2$O—C$\underline{H}_2$—, —C$\underline{H}_2$CH$_2$CN)

Example 4-2

Synthesis of Propylamino Body (Case of Molecular Weight of About 40,000)

To a 1 L autoclave were added 30 g of the cyanoethyl body, i.e, the compound (X) obtained in the above Example 4-1, 545 g of toluene, and 2.7 g of nickel (5136p manufactured by N. E. MCAT Company), and the whole was heated to 60° C. Pressurization was performed with ammonia until inner pressure reached 1 MPa and thereafter, hydrogen was introduced to achieve pressurization until the inner pressure reached 4.5 MPa, followed by reaction at 130° C. for 3 hours. After the reaction, the reaction solution was cooled to 80° C. and purging with nitrogen was repeated until ammonia odor disappeared. All the amount of the reaction solution was taken out and filtrated. After the filtrate was cooled to room temperature, hexane was added until crystals were precipitated. The crystals were collected by filtration and dried to obtain the following amine body (XI).

$^1$H-NMR (CDCl$_3$, internal standard: TMS) δ (ppm):
1.57 (4H, br, —OCH$_2$C$\underline{H}_2$C$\underline{H}_2$CH$_2$—O—),
1.72 (16H, quint, —CH$_2$C$\underline{H}_2$CH$_2$NH$_2$),
2.79 (16H, t, —CH$_2$CH$_2$C$\underline{H}_2$NH$_2$),
3.39 (4H, br, —OC$\underline{H}_2$CH$_2$CH$_2$C$\underline{H}_2$—O—),
3.50-3.80 (894H, m, —C$\underline{H}_2$O(C$\underline{H}_2$C$\underline{H}_2$O)$_n$H, C$\underline{H}$O(C$\underline{H}_2$C$\underline{H}_2$O)$_n$H, —C$\underline{H}_2$—OCH$_2$CH$_2$CH$_2$O—C$\underline{H}_2$—, —C$\underline{H}_2$CH$_2$CH$_2$NH$_2$)

GPC analysis (water system):
main fraction: 96.5%,
Mn: 28,201, Mw: 28,796, Mw/Mn: 1.021, Mp: 28,661

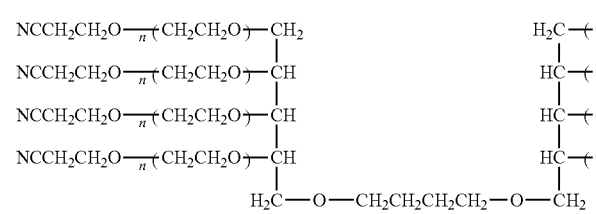

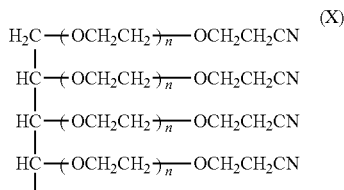

(X)

n ≈ 112

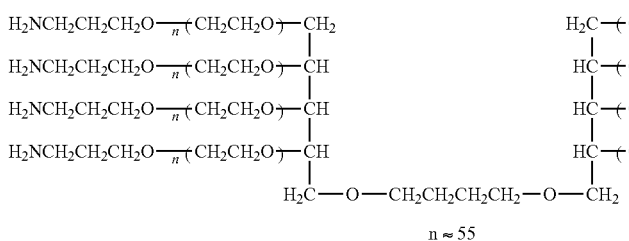
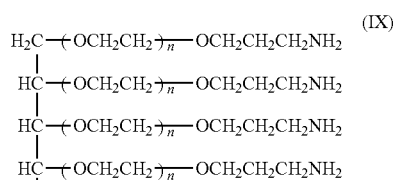

n ≈ 55

Example 5

Synthesis of Glutaric Acid NHS Body (Case of Molecular Weight of About 20,000)

To a 200 ml round-bottom flask fitted with a thermometer, a nitrogen-inlet tube, and a stirrer were added 50 g (2.5 mmol) of the compound (III) obtained in the above Example 1-6, 33 mg of BHT, 250 mg of sodium acetate, and 100 g of toluene, and PEG was dissolved under a nitrogen atmosphere. Thereafter, the whole was heated and refluxed at 110° C. to remove moisture. After cooling, 3.46 g (30.3 mmol) of glutaric anhydride was added, followed by reaction at 110° C. for 8 hours. Then, the reaction solution was cooled to 40° C. and 4.88 g (42.4 mmol) of N-hydroxysuccinimide and 8.34 g (40.4 mmol) of 1,3-dicyclohexylcarbodiimide were added, followed by reaction for 3 hours. After 3 hours, the reaction solution was filtrated and hexane was added to the filtrate until crystals were precipitated. The crystals were collected by filtration and dissolved in ethyl acetate under heating. Thereafter, hexane was added until crystals were precipitated and the crystals were collected by filtration and dried to obtain the objective compound (XII).

$^1$H-NMR (CDCl$_3$, internal standard: TMS) δ (ppm):
1.57 (4H, br, —OC$\underline{H_2}$C$\underline{H_2}$C$\underline{H_2}$CH$_2$—O—),
2.07 (16H, quint, —CH$_2$C$\underline{H_2}$CH$_2$C(O)O—),
2.50 (16H, t, —C$\underline{H_2}$CH$_2$CH$_2$C(O)O—),
2.72 (16H, t, —CH$_2$CH$_2$C$\underline{H_2}$C(O)O—),
2.84 (32H, br, —C(O)C$\underline{H_2}$C$\underline{H_2}$C(O)—),
3.40 (4H, br, —OC$\underline{H_2}$CH$_2$CH$_2$C$\underline{H_2}$—O—),
3.51-3.64 (1758H, m, —C$\underline{H_2}$O(C$\underline{H_2}$C$\underline{H_2}$O)$_n$H, CHO (C$\underline{H_2}$C$\underline{H_2}$O)$_n$H, —C$\underline{H_2}$—OCH$_2$CH$_2$CH$_2$CH$_2$O—C$\underline{H_2}$—,)
4.25 (16H, t, —OCH$_2$C$\underline{H_2}$OC(O)—), GPC analysis (DMF system):
main fraction: 97.7%,
Mn: 14,297, Mw: 14,650, Mw/Mn: 1.025, Mp: 15,160

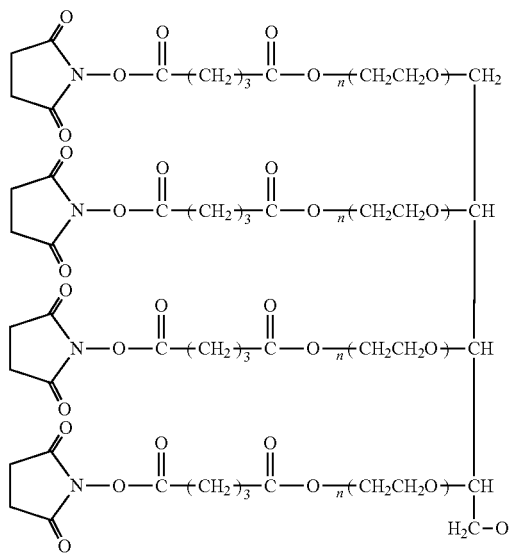
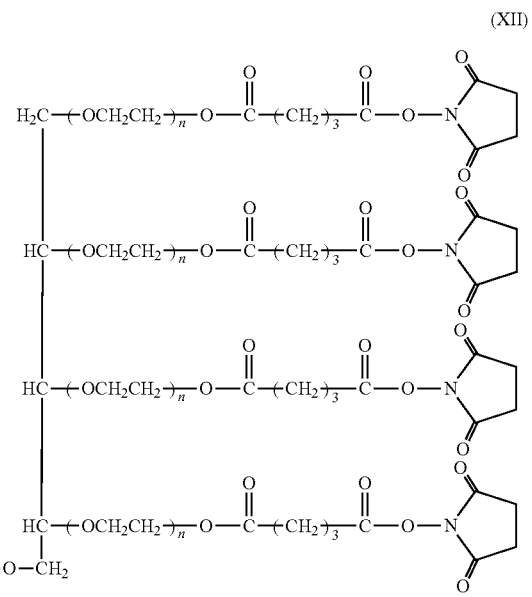

n ≈ 55

Comparative Example 1

Synthesis of the above compounds (I), (II), (III), and (IV) were conducted by the production methods described in Patent Literatures 1 and 2.

(Cases where L=n-butylene group, k=1, molecular weight of about 5,000, 10,000, 20,000, 40,000)

Comparative Example 1-1

Synthesis of Compounds (XIII) and (XIV): diisopropylidenexylitol

To a 5 L round-bottom flask fitted with a thermometer, nitrogen-inlet tube, and stirrer were charged 1,000 g of xylitol, 1,916 g of 2,2-dimethoxypropane, and 37.5 mg of p-toluenesulfonic acid monohydrate, and reaction was carried out at 65° C. while blowing nitrogen therein. The solvent of the reaction solution was distilled off, and the residue was purified by distillation (b.p. 108° C./0.15 mmHg) to obtain 1,527 g of an isomer mixture of 1,2,3,4-diisopropylidenexylitol (formula (XIII)) and 1,2,4,5-diisopropylidenexylitol (formula (XIV)).

$^1$H-NMR (CDCl$_3$, internal standard: TMS) δ (ppm):
1.37-1.44 (12H, m, —C(C$\underline{H}_3$)$_2$),
3.59-3.65 (1H, m, —C$\underline{H}$—O—),
3.81-3.90 (2H, m, —C$\underline{H}_2$—O—),
3.98-4.01 (1H, m, —C$\underline{H}$—O—),
4.04-4.10 (2H, m, —C$\underline{H}_2$—O—)
4.11-4.23 (1H, m, —C$\underline{H}$—O—)

3.99-4.06 (2H, m, —C$\underline{H}_2$—O—)
4.11-4.15 (1H, m, —C$\underline{H}$—O—)
7.36-7.54 (6H, m, $\underline{Ph}$—Si(—$\underline{Ph}$)—O—)
7.66-7.70 (4H, m, $\underline{Ph}$—Si(—$\underline{Ph}$)—O—)

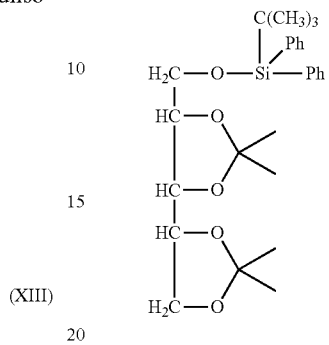

(XV)

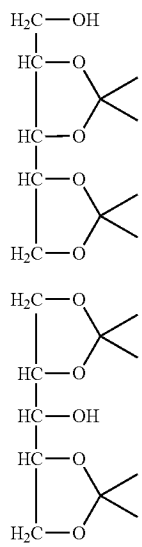

(XIII)

(XIV)

Comparative Example 1-3

Synthesis of Compound (XIII): 1,2,3,4-diisopropylidenexylitol

Into a 2 L round-bottom flask fitted with a thermometer, a nitrogen-inlet tube, and a stirrer were charged 500 g of 1,2,3,4-diisopropylidene-5-(t-butyldiphenylsilyl)xylitol and 440 g of dehydrated tetrahydrofuran, and the mixture was homogenize at room temperature while blowing nitrogen therein. After cooling to 20° C. or below, 1,270 ml of tetrabutylammonium fluoride (1 mol/L tetrahydrofuran solution) was added dropwise. After the dropwise addition, the temperature was returned to room temperature and the reaction was performed for 2 hours, and then the solvent was distilled off under reduced pressure. After the residue was dissolved with 2,000 g of ethyl acetate, the ethyl acetate layer was washed with purified water and dehydrated with magnesium sulfate, and then the solvent was distilled off. By column chromatography using chloroform and methanol as solvents and silica gel as a packing material, 150 g of 1,2,3,4-diisopropylidenexylitol (formula (XIII)) was obtained.

$^1$H-NMR (CDCl$_3$, internal standard: TMS) δ (ppm):
1.39, 1.44 (12H, s, —C$\underline{H}_3$),
3.62 (1H, dd, —C$\underline{H}$—O—),
3.08-3.89 (2H, m, —C$\underline{H}_2$—O—),
3.98-4.08 (1H, m, —C$\underline{H}$—O—, 2H, m, —C$\underline{H}_2$O—),
4.18-4.23 (1H, m, —C$\underline{H}$—O—)

Comparative Example 1-2

Synthesis of Compound (XV): 1,2,3,4-diisopropylidene-5-(t-butyldiphenylsilyl)xylitol Into a 2 L round-bottom flask fitted with a thermometer, nitrogen-inlet tube, and stirrer were charged 250 g of diisopropylidenexylitol (mixture of isomers) purified in 1-1, 1,000 g of dichloromethane, 26 g of 4-dimethylaminopyridine, and 109 g of triethylamine, and the mixture is dissolved at room temperature while blowing nitrogen therein. After cooling to 10° C. or lower, 297 g of t-butylchlorodiphenylsilane was added dropwise. After the dropwise addition, the temperature was returned to room temperature and reaction was performed for 2 hours. Then, the mixture was washed with a saturated aqueous sodium hydrogen carbonate solution and dehydrated with magnesium sulfate, and then the solvent was distilled off. 1,2,4,5-Diisopropylidenexylitol was removed at 135° C. under reduced pressure (0.2 mmHg) to obtain 200 g of 1,2,3,4-diisopropylidene-5-(t-butyldiphenylsilyl)xylitol (formula (XV)).

$^1$H-NMR (CDCl$_3$, internal standard: TMS) δ (ppm):
1.06 (9H, m, —Si—C—(C$\underline{H}_3$)$_3$)
1.37, 1.42, 1.43 (12H, s, —O—C—C$\underline{H}_3$)
3.72-3.82 (1H, m, —C$\underline{H}$—O—, —C$\underline{H}_2$—O—)
3.95 (1H, dd, —C$\underline{H}$—O—)

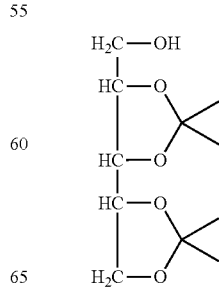

(XIII)

Comparative Example 1-4

Synthesis of Compound (XVI): 1,1'-butylene-bis(2,3,4,5-diisopropylidenexylitol)

After 130.3 g (0.56 mol) of 1,2,3,4-diisopropylidenexylitol and 1,650 g of dehydrated toluene were added to a 5,000 ml round-bottom flask fitted with a thermometer, a nitrogen-inlet tube, and a stirrer and dissolved each other under a nitrogen atmosphere, 65.4 g (0.58 mol) of potassium t-butoxide was added thereto, followed by stirring at room temperature for 30 minutes. On the other hand, 55.2 g (0.22 mol) of 1,4-butanediol dimethanesulfonate was dissolved in 660 g of dehydrated DMF and then the solution was added dropwise into the reaction solution at 40° C. or lower over a period of 30 minutes. After completion of the stepwise addition, the temperature was raised to 50° C. and the reaction was conducted for 6 hours. After completion of the reaction, the reaction solution was cooled and, after 1,100 g of ion-exchanged water was added and the whole was stirred for 20 minutes, the whole was allowed to stand and the aqueous layer was removed. A water-washing operation of adding 830 g of ion-exchanged water and allowing the whole to stand after stirring was repeated eight times to remove DMF and unreacted raw materials. After the water-washing, the organic layer was concentrated and dried with adding 27.6 g of magnesium sulfate, followed by filtration. The filtrate was again concentrated and purified by silica gel column chromatography (Wakogel C-200, eluent:ethyl acetate:hexane=10:3 (v/v)) to obtain 76.9 g of 1,1'-butylene-bis(2,3,4,5-diisopropylidenexylitol) (XVI) having the following structure.

$^1$H-NMR (CDCl$_3$, internal standard: TMS) δ (ppm):
1.39, 1.41, 1.42, 1.44 (24H, s, —O—C—C$\underline{H}_3$),
1.65 (4H, quint, —OCH$_2$C$\underline{H}_2$C$\underline{H}_2$CH$_2$—O—),
3.49 (4H, m, —OC$\underline{H}_2$CH$_2$CH$_2$C$\underline{H}_2$—O—),
3.54-3.58 (4H, m, —C$\underline{H}_2$—O—),
3.85 (2H, t, —C$\underline{H}$—O—),
3.89 (2H, dd, —C$\underline{H}$—O—),
4.02-4.07 (4H, m, —C$\underline{H}_2$—O—),
4.17 (2H, dd, —C$\underline{H}$—O—)

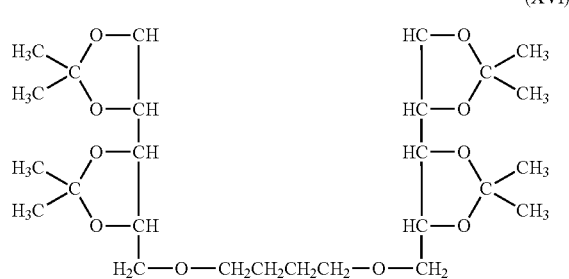

(XVI)

Comparative Example 1-5

Synthesis of 1,1'-Butylene-bisxylitol (V)

After 76.8 g (0.15 mol) of 1,1'-butylene-bis(2,3,4,5-diisopropylidenexylitol) (XVI) obtained in Comparative Example 1-4, 456 g of methanol, and 45 g of ion-exchanged water were added to a 1,000 ml round-bottom flask fitted with a thermometer, a nitrogen-inlet tube, and a stirrer and dissolved one another under a nitrogen atmosphere, 76.4 g of Dowex 50W-8H (manufactured by Dow Chemical Company) dispersed in 76 g of methanol was added thereto and the whole was heated and refluxed to remove acetone produced as a by-product in an azeotropic manner. The reaction solution was filtered and the filtrate was concentrated to obtain 53.6 g of the above-mentioned compound, 1,1'-butylene-bisxylitol (V).

$^1$H-NMR (D$_2$O, internal standard: TMS) δ (ppm):
1.66 (4H, quint, —OCH$_2$C$\underline{H}_2$C$\underline{H}_2$CH$_2$—O—),
3.56-3.75 (14H, m, —OC$\underline{H}_2$CH$_2$CH$_2$C$\underline{H}_2$—O—, —C$\underline{H}_2$—O—, —C$\underline{H}$—O—),
3.79-3.82 (2H, m, —C$\underline{H}$—O—),
3.91-3.93 (2H, m, —C$\underline{H}$—O—)

Comparative Example 1-6

Synthesis of Compound (I) (Case of Molecular Weight of 5,000)

Fifty-two grams of 1,1'-butylene-bisxylitol (V) obtained in Comparative Example 1-5 was warmed and, while washing it with 34 g of methanol, was charged into a 5 L autoclave. Subsequently, 4.9 g of potassium hydroxide and 10 g of ion-exchanged water were added to a 50 ml beaker to prepare an aqueous potassium hydroxide solution, which was then charged into the 5 L autoclave. Then, 500 g of dehydrated toluene was added thereto and an azeotropic dehydration operation was repeated three times at 80° C. under slightly reduced pressure. After the azeotropic dehydration, 1,423 g of dehydrated toluene was added and, after the inside of the system was replaced by nitrogen, 654 g (14.85 mol) of ethylene oxide was added thereto at 80 to 150° C. under a pressure of 1 MPa or less, followed by continuation of the reaction for another 1 hour. After the reaction, the whole was cooled to 60° C., 945 g of the reaction solution was taken out of the autoclave, and pH was adjusted to 7.5 with an 85% aqueous phosphoric acid solution to obtain the compound (I) mentioned above.

$^1$H-NMR (CDCl$_3$, internal standard: TMS) δ (ppm):
1.57 (4H, br, —OCH$_2$C$\underline{H}_2$C$\underline{H}_2$CH$_2$—O—),
2.66 (8H, br, —O$\underline{H}$),
3.40 (4H, br, —OC$\underline{H}_2$CH$_2$CH$_2$C$\underline{H}_2$—O—),
3.50-3.81 (430H, m, —C$\underline{H}_2$O(C$\underline{H}_2$C$\underline{H}_2$O)$_n$H, C$\underline{H}$O(C$\underline{H}_2$C$\underline{H}_2$O)$_n$H, —C$\underline{H}_2$—OCH$_2$CH$_2$CH$_2$O—C$\underline{H}_2$—)
GPC analysis (DMF system):
 main fraction: 100%,
 Mn: 3,971, Mw: 4,059, Mw/Mn: 1.022, Mp: 4,105
Molecular weight (TOF-MS); 4,991
Molecular weight (hydroxyl value); 5,097

Comparative Example 1-7

Synthesis of Compound (II) (Case of Molecular Weight of 10,000)

To about 1,345 g of the reaction solution remaining in the reaction vessel in Comparative Example 1-6 was added 370 g (8.40 mol) of ethylene oxide at 80 to 150° C. under a pressure of 1 MPa or less, followed by continuation of the reaction for another 1 hour. After the reaction, the whole was cooled to 60° C., 1,045 g of the reaction solution was taken out of the vessel, pH was adjusted to 7.5 with an 85% aqueous phosphoric acid solution, and toluene was removed by distillation to obtain the compound (II) mentioned above.

$^1$H-NMR (CDCl$_3$, internal standard: TMS) δ (ppm):
1.57 (4H, br, —OCH$_2$C$\underline{H}_2$C$\underline{H}_2$CH$_2$—O—),
2.365 (8H, br, —O$\underline{H}$), 3.40 (4H, s, —OCH₂CH₂CH₂CH₂—O—),
3.50-3.81 (878H, m, —CH₂O(CH₂CH₂O)ₙH, CHO(CH₂CH₂O)ₙH, —CH₂—OCH₂CH₂CH₂CH₂O—CH₂—)
GPC analysis (DMF system):
  main fraction: 100%,
  Mn: 7,264, Mw: 7,429, Mw/Mn: 1.023, Mp: 7,513
Molecular weight (TOF-MS); 10,033
Molecular weight (hydroxyl value); 10,158

Comparative Example 1-8

Synthesis of Compound (III) (Case of Molecular Weight of 20,000)

To about 524 g of the reaction solution remaining in the reaction vessel in Comparative Example 1-7 was added 182 g (4.13 mol) of ethylene oxide at 80 to 150° C. under a pressure of 1 MPa or less, followed by continuation of the reaction for another 1 hour. After the reaction, the whole was cooled to 60° C., 620 g of the reaction solution was taken out of the vessel, pH was adjusted to 7.5 with an 85% aqueous phosphoric acid solution, and toluene was removed by distillation to obtain the compound (III) mentioned above.
¹H-NMR (CDCl₃, internal standard: TMS) δ (ppm):
1.57 (4H, br, —OCH₂CH₂CH₂CH₂—O—),
2.57 (8H, br, —OH),
3.40 (4H, s, —OCH₂CH₂CH₂CH₂—O—),
3.50-3.81 (1774H, m, —CH₂O(CH₂CH₂O)ₙH, CHO(CH₂CH₂O)ₙH, —CH₂—OCH₂CH₂CH₂CH₂O—CH₂—)
GPC analysis (DMF system):
  main fraction: 99.3%,
  Mn: 13,965, Mw: 14,392, Mw/Mn: 1.031, Mp: 14,724
Molecular weight (TOF-MS); 20,083
Molecular weight (hydroxyl value); 20,225

Comparative Example 1-9

Synthesis of Compound (IV) (Case of Molecular Weight of 40,000)

To about 221 g of the reaction solution remaining in the reaction vessel in Comparative Example 1-8 was added 138 g (3.13 mol) of ethylene oxide at 80 to 150° C. under a pressure of 1 MPa or less, followed by continuation of the reaction for another 1 hour. After the reaction, the whole was cooled to 60° C., all the amount of the reaction solution was taken out of the vessel, pH was adjusted to 7.5 with an 85% aqueous phosphoric acid solution, and toluene was removed by distillation to obtain the compound (IV) mentioned above.
¹H-NMR (CDCl₃, internal standard: TMS) δ (ppm):
1.57 (4H, br, —OCH₂CH₂CH₂CH₂—O—),
2.589 (8H, br, —OH),
3.40 (4H, br, —OCH₂CH₂CH₂CH₂—O—),
3.50-3.81 (3598H, m, —CH₂O(CH₂CH₂O)ₙH, CHO(CH₂CH₂O)ₙH, —CH₂—OCH₂CH₂CH₂CH₂O—CH₂—)
GPC analysis (DMF system):
  main fraction: 97.3%,
  Mn: 28,595, Mw: 29,392, Mw/Mn: 1.028, Mp: 30,103
Molecular weight (TOF-MS); 41,450
Molecular weight (hydroxyl value); 38,590

Comparative Example 2-1

Synthesis of Cyanoethyl Body (Case of Molecular Weight of About 10,000)

To a 500 ml round-bottom flask fitted with a thermometer, a nitrogen-inlet tube, a stirrer, and a cooling tube were added 30 g (3 mmol) of the compound (II) obtained in the above Comparative Example 1-7 and 30 g of ion-exchanged water, and the whole was heated to 40° C. to achieve dissolution. After the dissolution, the whole was cooled to 10° C. or lower and 3 g of a 50% aqueous potassium hydroxide solution was added thereto. Subsequently, while the temperature was kept at 5 to 10° C., 25.5 g (480 mmol) of acrylonitrile was added dropwise over a period of 2 hours. After completion of the dropwise addition, the reaction was further conducted for 4 hours and, after 30 g of ion-exchanged water was added, neutralization was achieved by adding 1.8 g of an 85% aqueous phosphoric acid solution. After 45 g of ethyl acetate was added and the whole was stirred, it was allowed to stand and an upper ethyl acetate layer was discarded. The extraction with ethyl acetate was repeated nine times. After completion of the extraction, extraction with 150 g of chloroform was performed. The resulting chloroform layer was dried over 15 g of magnesium sulfate and, after filtration, was concentrated. The concentrated liquid was dissolved with adding 90 g of ethyl acetate, and hexane was added until crystals were precipitated. The crystals were collected by filtration and again dissolved in 90 g of ethyl acetate under heating and, after cooling to room temperature, hexane was added until crystals were precipitated. The crystals were collected by filtration and dried to obtain the cyanoethyl body (VI) mentioned above.
¹H-NMR (CDCl₃, internal standard: TMS) δ (ppm):
1.57 (4H, br, —OCH₂CH₂CH₂CH₂—O—),
2.63 (16H, t, —CH₂CH₂CN),
3.39 (4H, br, —OCH₂CH₂CH₂CH₂—O—),
3.50-3.80 (894H, m, —CH₂O(CH₂CH₂O)ₙH, CHO(CH₂CH₂O)ₙH, —CH₂—OCH₂CH₂CH₂CH₂O—CH₂—, —CH₂CH₂CN)

Comparative Example 2-2

Synthesis of Propylamino Body (Case of Molecular Weight of About 10,000)

To a 1 L autoclave were added 13 g of the cyanoethyl body, i.e, the compound (VI) obtained in the above Comparative Example 2-1, 560 g of toluene, and 1.2 g of nickel (5136p manufactured by N. E. MCAT Company), and the whole was heated to 60° C. Pressurization was performed with ammonia until inner pressure reached 1 MPa and thereafter, hydrogen was introduced to achieve pressurization until the inner pressure reached 4.5 MPa, followed by reaction at 130° C. for 3 hours. After the reaction, the reaction solution was cooled to 80° C. and purging with nitrogen was repeated until ammonia odor disappeared. All the amount of the reaction solution was taken out and filtrated. After the filtrate was cooled to room temperature, hexane was added until crystals were precipitated. The crystals were collected by filtration and dried to obtain the amine body (VII) mentioned above.
¹H-NMR (CDCl₃, internal standard: TMS) δ (ppm):
1.57 (4H, br, —OCH₂CH₂CH₂CH₂—O—),
1.72 (16H, quint, —CH₂CH₂CH₂NH₂),
2.79 (16H, t, —CH₂CH₂CH₂NH₂),
3.39 (4H, br, —OCH₂CH₂CH₂CH₂—O—),
3.50-3.80 (894H, m, —CH₂O(CH₂CH₂O)ₙH, CHO(CH₂CH₂O)ₙH, —CH₂—OCH₂CH₂CH₂CH₂O—CH₂—, —CH₂CH₂CH₂NH₂)

GPC analysis (water system):
  main fraction: 97.9%,
  Mn: 6,334, Mw: 6,477, Mw/Mn: 1.022, Mp: 6,571

Comparative Example 3

Synthesis of Glutaric Acid NHS Body (Case of Molecular Weight of About 20,000)

To a 200 ml round-bottom flask fitted with a thermometer, a nitrogen-inlet tube, and a stirrer were added 25 g (1.25 mmol) of the compound (III) obtained in Comparative Example 1-8, 25 mg of BHT, 125 mg of sodium acetate, and 60 g of toluene, and PEG was dissolved under a nitrogen atmosphere. Thereafter, the whole was heated and refluxed at 110° C. to remove moisture. After cooling, 1.71 g (15.0 mmol) of glutaric anhydride was added thereto, followed by reaction at 110° C. for 8 hours. Then, the reaction solution was cooled to 40° C. and 3.45 g (30.0 mmol) of N-hydroxysuccinimide and 4.33 g (21.0 mmol) of 1,3-dicyclohexylcarbodiimide were added, followed by reaction for 3 hours. After 3 hours, the reaction solution was filtrated and hexane was added to the filtrate until crystals were precipitated. The crystals were collected by filtration and dissolved in ethyl acetate under heating. Thereafter, hexane was added until crystals were precipitated and the crystals were collected by filtration and dried to obtain the objective compound (XII).
$^1$H-NMR (CDCl$_3$, internal standard: TMS) δ (ppm):
1.57 (4H, br, —OCH$_2$CH$_2$CH$_2$CH$_2$—O—),
2.07 (16H, quint, —CH$_2$CH$_2$CH$_2$C(O)O—),
2.50 (16H, t, —CH$_2$CH$_2$CH$_2$C(O)O—),
2.72 (16H, t, —CH$_2$CH$_2$CH$_2$C(O)O—),
2.84 (32H, br, —C(O)CH$_2$CH$_2$C(O)—),
3.40 (4H, br, —OCH$_2$CH$_2$CH$_2$CH$_2$—O—),
3.51-3.64 (1758H, m, —CH$_2$O(CH$_2$CH$_2$O)$_n$H, CHO(CH$_2$CH$_2$O)$_n$H, —CH$_2$—OCH$_2$CH$_2$CH$_2$CH$_2$O—CH$_2$—,)
4.25 (16H, t, —OCH$_2$CH$_2$OC(O)—),
GPC analysis (DMF system):
  main fraction: 97.5%,
  Mn: 14,711, Mw: 15,116, Mw/Mn: 1.028, Mp: 15,635

Table 1 summarizes the purity and the total yield of the propylamino body (VII) obtained in Example 2-2 and Comparative Example 2-2 according to the production method.

TABLE 2

| Compound | | Molecular weight | Terminal functional group | Mw/Mn |
|---|---|---|---|---|
| Example 1-4 | (I) | 5,000 | Hydroxyl group | 1.017 |
| Comparative Example 1-6 | | | | 1.022 |
| Example 1-5 | (II) | 10,000 | | 1.019 |
| Comparative Example 1-7 | | | | 1.023 |
| Example 1-6 | (III) | 20,000 | | 1.025 |
| Comparative Example 1-8 | | | | 1.031 |
| Example 1-7 | (IV) | 40,000 | | 1.020 |
| Comparative Example 1-9 | | | | 1.028 |
| Example 2-2 | (VII) | 10,000 | Propylamino group | 1.017 |
| Comparative Example 2-2 | | | | 1.022 |
| Example 5 | (XII) | 20,000 | Glutaric acid NHS group | 1.025 |
| Comparative Example 3 | | | | 1.028 |

In the conventional production method, for example, three steps were required to obtain a highly pure protected body of xylitol and column chromatography was used in the purification step, so that a large decrease in yield was observed. On the other hand, in the production method of the invention, the highly pure protected body of xylitol is produced in one step without requiring a special purification step, and therefore the total molar yield can be significantly improved. It was also shown that the multi-arm type polyethylene glycol derivative of the invention and the intermediate thereof have equal quality in polydispersity and purity.

INDUSTRIAL APPLICABILITY

According to the present invention, it is possible to provide a method capable of industrially producing a highly pure multi-arm type polyethylene glycol derivative having a narrow molecular weight distribution, which is suitable for use as a material in DDS and the biological and medical fields, in high yields.

While the present invention has been described in detail and with reference to specific embodiments thereof, it will be apparent to one skilled in the art that various changes and modifications can be made therein without departing from the spirit and scope thereof.

TABLE 1

| | Examples | | | | |
|---|---|---|---|---|---|
| Step | Example 1-1 | Example 1-2 | Example 1-3 | Example 1-5 | Example 2-2 |
| Total molar yield | 85% | 55% | 47% | 42% | 34% |
| NMR purity | 99% | 98% | 99% | 99%* | 94% |

| | Comparative Examples | | | | | | |
|---|---|---|---|---|---|---|---|
| Step | Comparative Example 1-1 | Comparative Example 1-2 | Comparative Example 1-3 | Comparative Example 1-4 | Comparative Example 1-5 | Comparative Example 1-7 | Comparative Example 2-2 |
| Total molar yield | 95% | 38% | 23% | 15% | 10% | 9% | 7% |
| NMR purity | 80% | 80% | 99% | 98% | 99% | 100%* | 90% |

*GPC purity

Table 2 summarizes the results of the polydispersity (Mw/Mn) of the main fraction obtained from the GPC analysis in Examples 1-4 to 7, 2-2, and 5 and Comparative Examples 1-6 to 9, 2-2, and 3.

The present application is based on Japanese Patent Application No. 2018-59150 filed on Mar. 27, 2018, and the contents thereof are incorporated herein by reference.

The invention claimed is:

1. A method for producing a multi-arm type polyethylene glycol derivative represented by the following formula (1), wherein the following step (A), step (B), step (C), step (D), and step (E) are carried out in this order:

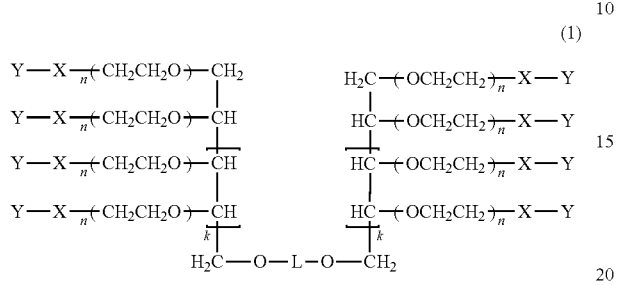

(1)

wherein, in the formula (1),
- L is a group selected from the group consisting of a linear or branched alkylene group having 3 to 8 carbon atoms, a substituted or unsubstituted arylene group having 6 to 12 carbon atoms and a cycloalkylene group having 6 to 12 carbon atoms,
- k represents 1 or 2,
- n represents an average molar number of oxyethylene groups added and n represents an integer between 3 and 600,
- X represents an alkylene group which may have a single bond, an ester bond, a urethane bond, an amide bond, an ether bond, a carbonate bond, a secondary amino group, a urea bond, a thioether bond, or a thioester bond in a chain or at a terminal, and
- Y represents a chemically reactive functional group;

Step (A): a step of protecting an even number of hydroxyl groups, while leaving only the hydroxyl group at the 1-position of a polyhydric alcohol having an odd number of hydroxyl groups, other than the hydroxyl group at the 1-position by cyclic benzylidene acetalization, Step (B): a step of linking two molecules of the compound obtained in the step (A) to a compound represented by the following formula (2) by an etherification reaction to obtain a compound, and purifying the obtained compound by recrystallization in dimethylformamide:

wherein, in the formula (2),
- L represents a group selected from the group consisting of a linear or branched alkylene group having 3 to 8 carbon atoms, a substituted or unsubstituted arylene group having 6 to 12 carbon atoms and a cycloalkylene group having 6 to 12 carbon atoms, and
- A represents a halogen atom selected from chlorine, bromine or iodine, or a sulfone-based leaving group, Step (C): a step of deprotecting the cyclic benzylidene acetal structure at the terminal of the compound obtained in the step (B), where 8 hydroxyl groups are formed in the case of k=1 and 12 hydroxyl groups are formed in the case of k=2, Step (D): a step of polymerizing 3 to 600 mol of ethylene oxide to each hydroxyl group of the compound obtained in the step (C) to obtain a multi-arm type polyethylene glycol derivative, and Step (E): a step of functionalizing the hydroxyl group at the terminal of the multi-arm type polyethylene glycol derivative obtained in the step (D).

2. The method according to claim 1, wherein the step (A) is carried out using an acidic solution as a solvent.

3. The method according to claim 1, wherein the step (C) is carried out under an acidic condition.

* * * * *